United States Patent
Hua

(10) Patent No.: US 10,906,033 B2
(45) Date of Patent: Feb. 2, 2021

(54) SYNTHESIS AND APPLICATION OF CHIRAL SUBSTITUTED POLYVINYLPYRROLIDINONES

(71) Applicant: Kansas State University Research Foundation, Manhattan, KS (US)

(72) Inventor: Duy H. Hua, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 272 days.

(21) Appl. No.: 16/089,609

(22) PCT Filed: Mar. 28, 2017

(86) PCT No.: PCT/US2017/024533
§ 371 (c)(1),
(2) Date: Sep. 28, 2018

(87) PCT Pub. No.: WO2017/172763
PCT Pub. Date: Oct. 5, 2017

(65) Prior Publication Data

US 2020/0306737 A1 Oct. 1, 2020

Related U.S. Application Data

(60) Provisional application No. 62/314,227, filed on Mar. 28, 2016.

(51) Int. Cl.
| | | |
|---|---|---|
| *C08F 26/10* | (2006.01) | |
| *B01J 23/52* | (2006.01) | |
| *B01J 31/28* | (2006.01) | |
| *C07B 41/02* | (2006.01) | |
| *C07B 53/00* | (2006.01) | |
| *C07B 41/04* | (2006.01) | |
| *B01J 31/06* | (2006.01) | |
| *B01J 23/89* | (2006.01) | |

(52) U.S. Cl.
CPC ............. *B01J 31/061* (2013.01); *B01J 23/52* (2013.01); *B01J 23/8926* (2013.01); *B01J 31/28* (2013.01); *C07B 41/02* (2013.01); *C07B 41/04* (2013.01); *C07B 53/00* (2013.01); *C08F 26/10* (2013.01); *B01J 2231/763* (2013.01); *B01J 2531/0211* (2013.01); *C07B 2200/07* (2013.01)

(58) Field of Classification Search
None
See application file for complete search history.

(56) References Cited

U.S. PATENT DOCUMENTS

| | | |
|---|---|---|
| 4,006,023 A | 2/1977 | McLaughlin et al. |
| 5,306,561 A | 4/1994 | Frechet et al. |
| 9,601,758 B2 * | 3/2017 | Put ........................ H01M 4/587 |
| 2007/0287825 A1 | 12/2007 | Baggio et al. |
| 2011/0028641 A1 | 2/2011 | Wang et al. |
| 2011/0034654 A1 | 2/2011 | Hansen et al. |
| 2015/0340687 A1 | 11/2015 | Put et al. |

OTHER PUBLICATIONS

International Search Report and Written Opinion dated Jun. 20, 2017, in PCT/US2017/024533, filed Mar. 28, 2017.

* cited by examiner

*Primary Examiner* — Kamal A Saeed
(74) *Attorney, Agent, or Firm* — Hovey Williams LLP

(57) ABSTRACT

Chiral polyvinylpyrrolidinone (CSPVP), complexes of CSPVP with a core species, such as a metallic nanocluster catalyst, and enantioselective oxidation reactions utilizing such complexes are disclosed. The CSPVP complexes can be used in asymmetric oxidation of diols, enantioselective oxidation of alkenes, and carbon-carbon bond forming reactions, for example. The CSPVP can also be complexed with biomolecules such as proteins, DNA, and RNA, and used as nanocarriers for siRNA or dsRNA delivery.

23 Claims, 9 Drawing Sheets

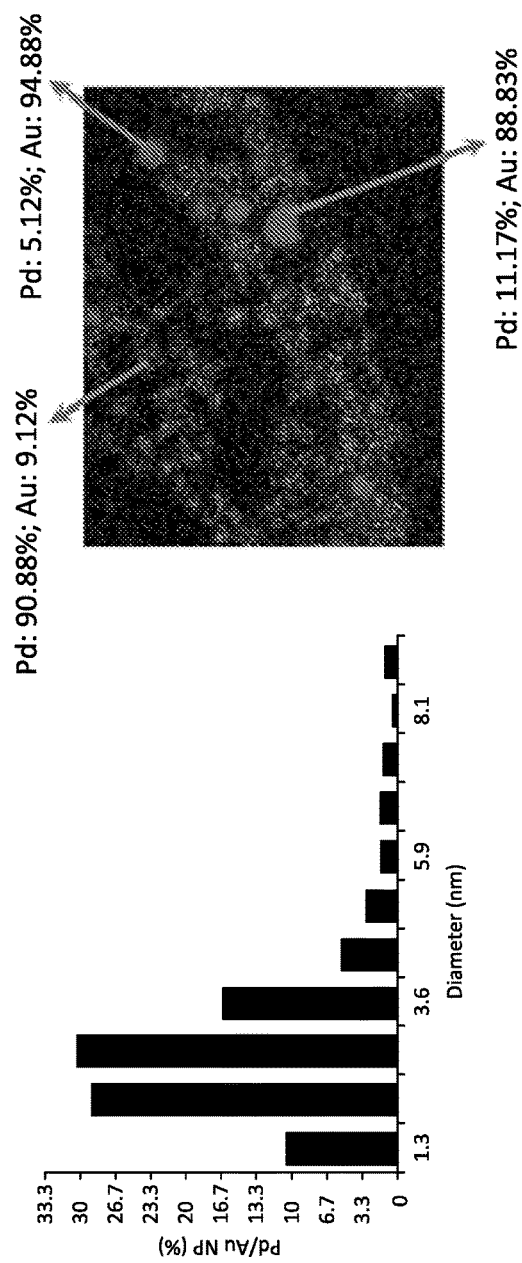
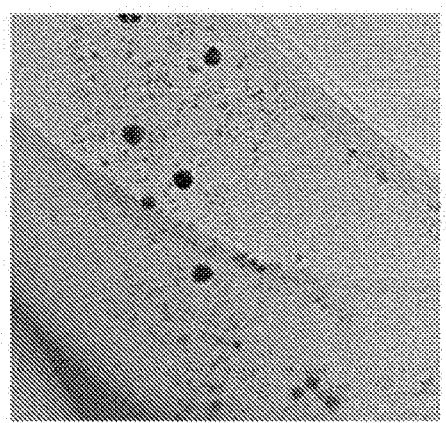
Fig. 1A.
Fig. 1B.
Fig. 1C.

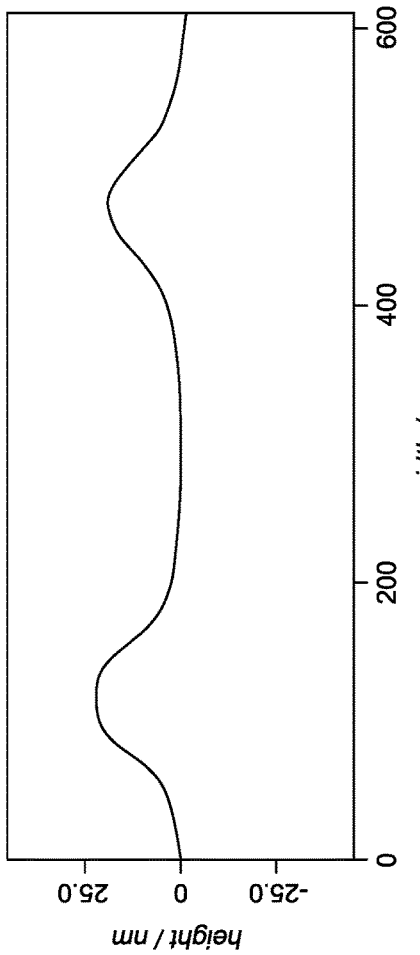
Fig. 4A.
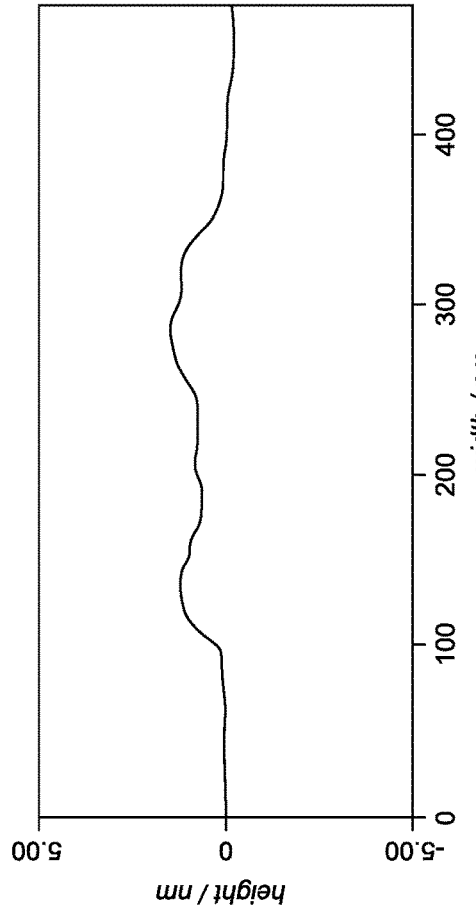
Fig. 4B.
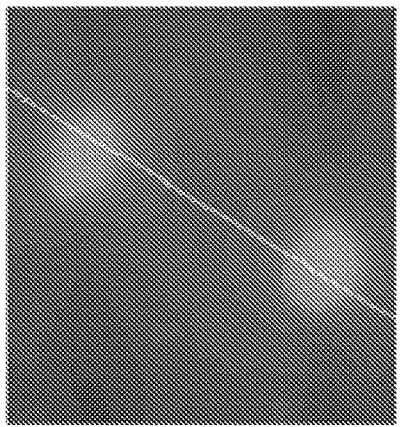
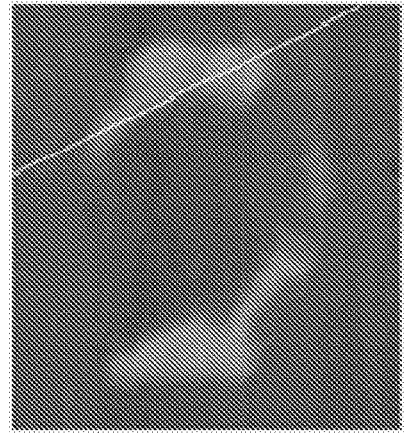

SYNTHESIS AND APPLICATION OF CHIRAL SUBSTITUTED POLYVINYLPYRROLIDINONES

CROSS-REFERENCE TO RELATED APPLICATIONS

The present application is a national stage entry under 35 U.S.C. 371 of International Patent Application No. PCT/US2017/024533, filed Mar. 28, 2017, which claims the priority benefit of U.S. Provisional Patent Application Ser. No. 62/314,227, filed Mar. 28, 2016, entitled SYNTHESIS AND APPLICATION OF CHIRAL SUBSTITUTED POLYVINYLPYRROLIDINONES, incorporated by reference in its entirety herein.

BACKGROUND OF THE INVENTION

Field of the Invention

The present invention is generally directed toward a chiral substituted polyvinylpyrrolidinone compound that can be used as stabilizers for nanoparticle catalysts, among other things such as nanodelivery. The polymer/catalyst complex can be used to facilitate a variety of enantioselective oxidation reactions.

Description of the Prior Art

The enantioselective synthesis of chiral molecules has been the subject of intense investigation for several decades. In fact, enantioselective functionalization of alkenes has been one of the most studied reactions in organic synthesis. Particularly, catalytic asymmetric dihydroxylation has been intensely pursued by synthetic organic chemists, and the Sharpless asymmetric dihydroxylation process is a major breakthrough and one of the highest achievements in asymmetric catalysis. However, there are drawbacks in the procedure and they include a lower enantioselectivity in Z-1,2-disubstituted alkenes and toxicity and volatility of the osmium catalyst. Hence, catalytic reactions including enzyme-osmate catalytic dihydroxylation and homogeneous palladium-catalyzed difunctionalization reactions of alkenes were subsequently developed. However, palladium-catalyzed asymmetric dihydroxylation is rare. Other asymmetric dihydroxylations with osmium-free catalysts including $RuO_4$, $KMnO_4$, iron complexes, and enzymes along with non-asymmetric oxidants such as molybdenum complexes, $(NH_4)_2Ce(NO_3)_6$, $SeO_2$, $NaIO_4$, $PhI(OAc)_2$, and oxone have also been investigated. Despite efforts that have been devoted to the design and synthesis of chiral amine ligands for the asymmetric oxidation of Z-1,2-disubstituted alkenes in the past years, the enantiomeric excess (ee) remains low. The non-catalytic process in some cases limits its application in industrial settings.

Although organic transformation reactions using bimetallic catalysts, without studying enantio- or stereo-selectivity, including Pd/Au in the oxidation of alcohols, formic acid oxidation, aldehyde oxidation, benzylic C—H oxidation, Ullmann coupling, Suzuki coupling reaction, tandem oxidation-Michael addition reaction, Pt/Pd—$H_2O_2$ epoxidation of olefins, and stabilization of Pd/Au in chiral glutathione or chitosan have been reported, enantioselective oxidation of cycloalkenes from a combination of bimetallic alloy catalysts and polymers containing asymmetric centers are unprecedented.

SUMMARY OF THE INVENTION

According to one embodiment of the present invention, a chiral substituted polyvinylpyrrolidinone compound is provided. The chiral substituted polyvinylpyrrolidinone compound can be used in the formation of complexes with, for example, a core species elected from the group consisting of nanoparticulate materials, proteins, DNA, and RNA. In certain embodiments, the chiral substituted polyvinylpyrrolidinone compound comprises an acetonide moiety attached to the pyrrolidine ring According to another embodiment of the present invention, a process for asymmetrically oxidizing organic molecules is provided. The process comprises reacting the organic molecule, which may include alkenes, cycloalkanediols, alkanediols, and cycloalkanes, with one or more reagents in the presence of a complex formed from a chiral substituted polyvinylpyrrolidinone compound bound with a metallic nanocluster.

BRIEF DESCRIPTION OF THE DRAWINGS

FIG. 1A is a representative TEM image of Pd/Au (3:1)-CSPVP (the scale bar is 20 nm);

FIG. 1B is a histogram from analysis of TEM images showing diameters of the catalysts;

FIG. 1C is an EDS image of the catalysts, and the values showing compositions (in percentages) of Pd and Au in different areas;

FIG. 4A is an AFM image of α-hydroxy-PVP;

FIG. 4B is an AFM image of the encapsulation of α-hydroxy-PVP/dsDNA;

DETAILED DESCRIPTION OF THE PREFERRED EMBODIMENT

Figure 2:
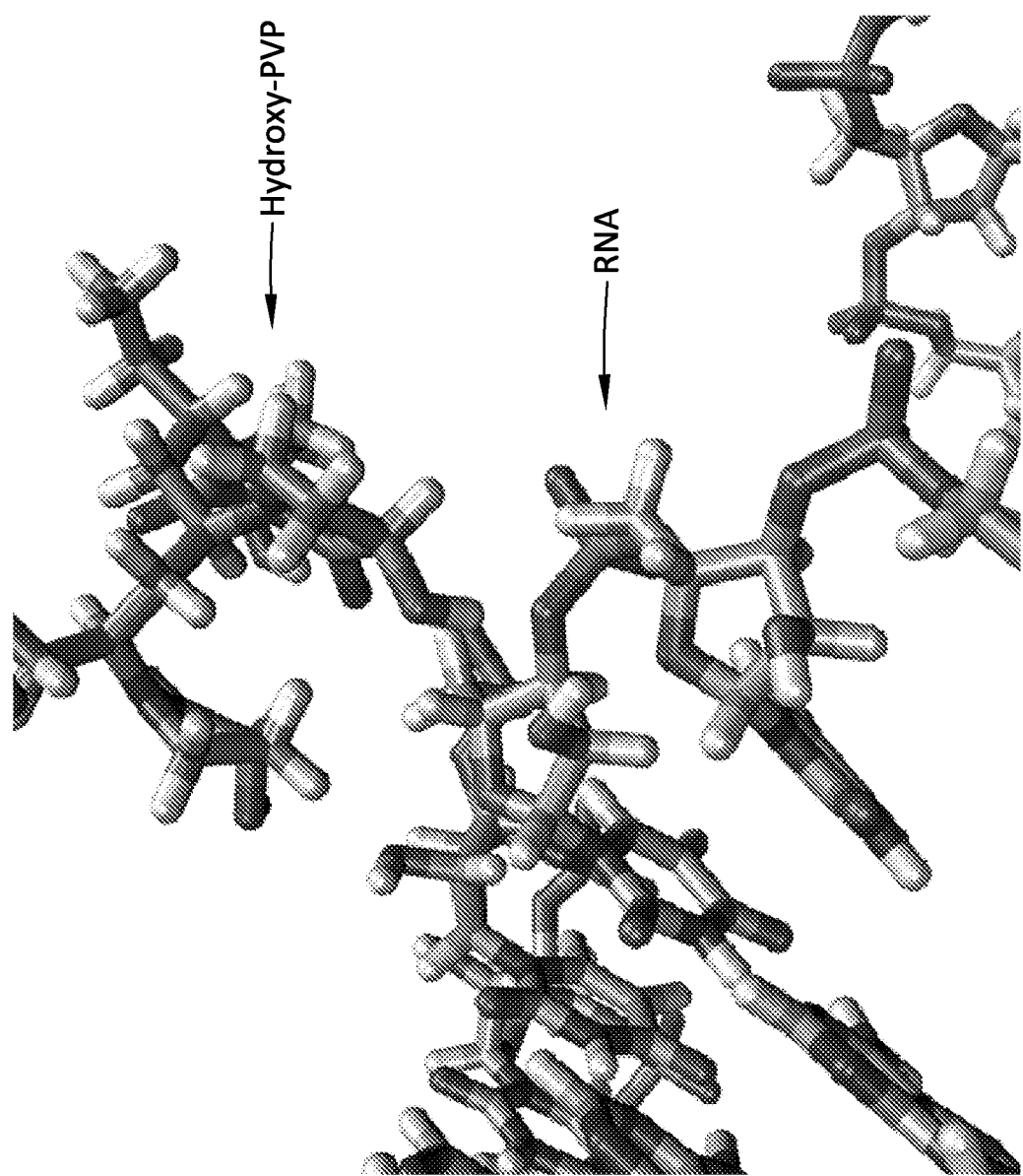
FIG. 2 is a model illustrating one of the hydrogen bondings between α-hydroxy PVP and siRNA.

One embodiment of the present invention pertains to the synthesis of chiral polymers from substituted 1-vinylpyrrolidinones, and in particular (5R)-5-substituted 1-vinylpyrrolidinones, hereinafter referred to as CSPVP. The CSPVP can be used as stabilizers of nanoparticle catalysts, especially bimetallic nanoparticle catalysts, such as those described in greater detail below.

According to one embodiment, the CSPVP has a general formula of

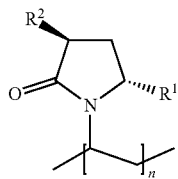

wherein one of $R^1$ and $R^2$ comprises a functional group having at least 1 carbon atoms selected from the group consisting of alcohols, ethers, aliphatic hydrocarbons, aromatic hydrocarbons, and combinations thereof, and the other of $R^1$ and $R^2$ is H or OH, and n is greater than 100. In certain embodiments, one of $R^1$ and $R^2$ comprises a functional group having at least 5 carbon atoms, at least 8 carbon atoms, or at least 10 carbon atoms. In other embodiments, one of $R^1$ and $R^2$ comprise from 3 to 30 carbon atoms, from 5 to 25 carbon atoms, or from 8 to 20 carbon atoms. In certain embodiments, n is at least 250, at least 300, or at least 400. In particular embodiments, n is from about 100 to about 1000, from about 250 to about 800, or from about 300 to about 700. In certain embodiments, the CSPVP compound has a molecular weight of at least 50,000, at least 60,000, or at least 70,000. In particular embodiments, the CSPVP compound has a molecular weight of from about 50,000 to about 120,000, from about 60,000 to about 110,000, or from about 70,000 to about 100,000. In still other embodiments, $R^1$ is selected from the group consisting of $CH_2Ph$, $CH_2O$-t-Bu, $CHCH_3CH_3$, $CH_2(1$-Naph$)$, $CH_2OH$, $CH_2OCHPh_2$, or $R^2$ is selected from the group consisting of OR' (where R' is an ester or alkyl group), $CH_3$, an alkyl group, $CH_2OH$, and the other of $R^1$ and $R^2$ is H or OH.

According to another embodiment, the CSPVP comprises an acetonide moiety attached to the pyrrolidine ring. In certain such embodiments, the CSPVP has a formula of

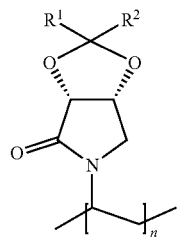

wherein each of $R^1$ and $R^2$ is independently selected from aliphatic or aromatic functional groups, and preferably each is independently selected from the group consisting of $CH_3$, $CH_2CH_3$, and Ph (phenyl), and n is greater than 100.

According to one embodiment, the synthesis of CSPVPs began with the synthesis of enantiopure 5-substituted-2-pyrrolidinones, which were made from chiral α-amino acids. The purchased N-Boc-L-amino acids were recrystallized twice from ethyl acetate and hexane to obtain pure amino acids having the highest optical rotations before use. According to Scheme 1, below, N-Boc L-(S)-amino acids such as 1-4 were separately coupled with Meldrum's acid followed by reduction of the ketone function, cyclization, and removal of the Boc group to give enantiopure 4b, 5b, 6b, and 7b in excellent overall yields. Boc-L-1-naphthylalanine was purchased from PepTech Co. (Burlington, Mass.). These lactams were converted to N-vinyllactams 9-12, separately by the treatment of $Na_2PdCl_4$/vinyl acetate. For instance, utilizing the dispersion polymerization method, monomer 9 was polymerized by azobisisobutyronitrile (AIBN; 0.4%) and copolymer 13a (2% by weight) to give polymer 14 having molecular weight (MW) of 76,000 (determined by gel permeation chromatography using TSK-gel GMHx1 column and water as solvent with a flow rate of 1 mL/min). Copolymer 13a was prepared from the polymerization of 9 and vinyl acetate with a catalytic amount of AIBN in acetone at 60° C. Similarly, polymers 15-17 were synthesized from monomers 10-12, respectively (MWs are listed in Scheme 1). Both R- and S-stereochemistry are likely present in the stereogenic center (marked with * in the polymers) of the alkane backbone of the polymers, and they are not identifiable. Presumably, this stereogenic center of the polymers (can be isotactic, atactic, and syndiotactic) has lesser effect on the enantioselective catalytic oxidation reactions, which are discussed in greater detail below. Polymer 15 was treated with trifluoroacetic acid (TFA) to give polymer 18, and the hydroxyl function was alkylated with NaH and benzhydryl bromide to give polymer 19. Molecular weight determination and NMR spectral data show ~72% of the hydroxyl groups of 18 were alkylated. It is believed that a longer reaction time of the alkylation reaction will likely provide a greater amounts of alkylation. Importantly, the hydroxyl moiety of 18 may be converted to other functional groups including amine, amide, and diphenylphosphine. The polymers are used as chiral supports (or stabilizers) in various oxidation reactions described below. The polymers were characterized by IR, $^1H$ and $^{13}C$ NMR, UV (for UV active polymers), gel permeation chromatography (for MW determination), and circular dichroism (CD) spectroscopy. To study whether an additional functional group can be introduced into the lactam ring of CSPVP, lactam 6a was converted to 20 by the sequence of reactions: (i) selenylation with lithium diisopropylamide (LDA) in THF and phenylselenyl bromide; and (ii) dehydroselenylation with sodium periodate in dioxane-water. The success in synthesis of 20 may lead to various disubstituted chiral lactams by 1,4-addition reactions.

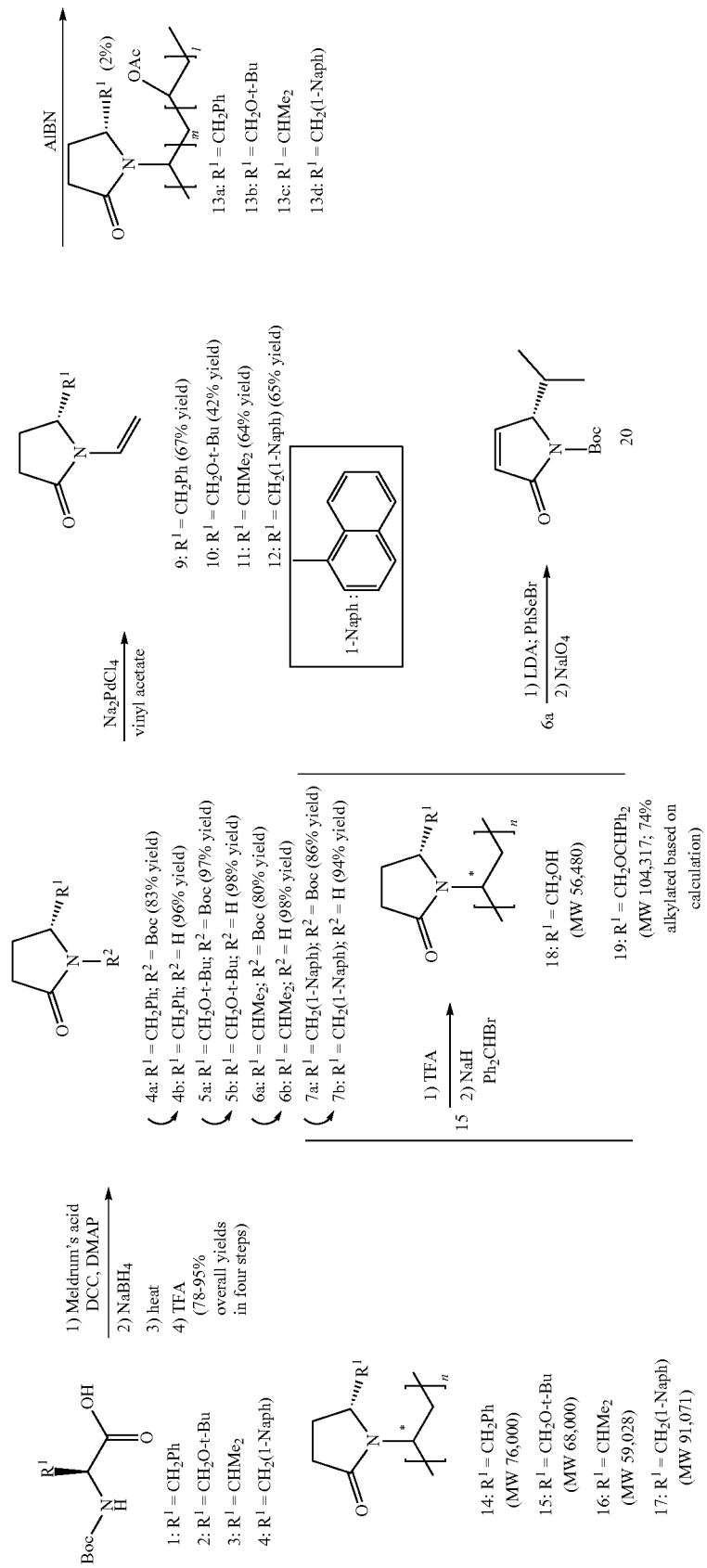

Nanoparticle clusters (also referred to as nanoclusters) are useful as catalysts in numerous chemical reactions. However, the catalytic activity of the nanoparticle cluster is largely dependent upon the material not aggregating into larger particles, which many nanoparticle clusters will naturally tend to do in certain reaction environments. The CSPVP molecules described herein can be used as stabilizers for various core species including nanoparticle clusters and biomolecules such as DNA, RNA and proteins.

Nanoparticle clusters can be prepared by a number of methods including molecular beams, chemical reduction, thermal decomposition of transition metal complexes, ion implantation, electrochemical synthesis, radiolysis, sonochemical synthesis, and biosynthesis. In one embodiment, the nanoparticle clusters comprise a metal. In preferred embodiments, the metal is present in its elemental, or zero valence, form, either alone as a monometal catalyst or alloyed with other metals. In particular embodiments, the nanoclusters comprise one or more transition metals, especially a transition metal selected from the group consisting of Au, Pd, Cu, Ce, Mo, Ni, Ru, W, and Fe. In certain embodiments, the nanoclusters are generally spherical and exhibit average particle diameters of from about 1 to about 100 nm, from about 2 to about 50 nm, or from about 3 to about 25 nm.

In one particular embodiment, the nanoparticles comprise bimetallic materials. Exemplary bimetallic materials comprise those including Au as one of the metallic species due to its high electron-positivity, catalytic activity, and synergistic electronic effects, such as Pd/Au, Cu/Au, Ce/Au, Mo/Au, W/Au, Ni/Au, Ru/Au, and Fe/Au. The preparation of CSPVP-stabilized Pd/Au nanoparticle clusters is exemplified by the following synthesis scheme.

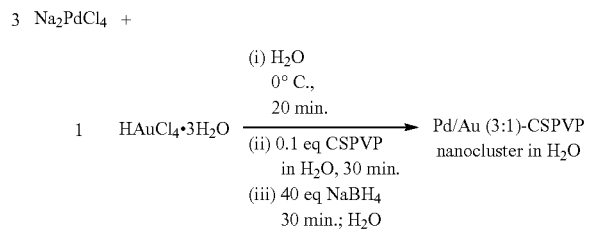

The Pd/Au catalysts were prepared by the treatment of Na$_2$PdCl$_4$ (3 equiv.), HAuCl$_4$ (1 equiv.), and CSPVP (molecule 14 from Scheme 1, 0.14 equiv.) in water with NaBH$_4$ and then filtered through a Vivaspin 20 (Sartorius Inc.) centrifugal filter device (with a 3,000 MWCO), and washed with deionized water twice to remove low MW inorganic materials. The resulting nanoparticle clusters were dissolved in water, lyophilized to give Pd/Au (3:1)/CSPVP 14, which was subjected to various characterization and oxidation reactions. PVP having a molecular weight of approximately 42,000 was also used in the aforementioned nanocluster formation reaction, as a racemic stabilizer for control experiments.

Different ratios of Pd and Au (such as 2:1 and 1:1) and other chiral supports were also prepared, as were Cu/Au and Fe/Au nanoclusters in chiral supports. The Pd/Au (3:1) nanoclusters stabilized by CSPVP (or PVP) were characterized by IR, UV-vis, CD, CD-UV, TEM (transmission electron microscopy), AFM (atomic force microscopy), EDS (energy-disperse X-ray microanalysis), XPS (X-ray photoelectron spectroscopy), and EXAFS (extended X-ray absorption fine structure). The TEM graph and histogram analysis (FIGS. 1A and 1B) reveal average sizes of Pd/Au (3:1) stabilized by the CSPVP 14. The average diameter of the spherical nanoclusters is ~3.4±1.4 nm. FIG. 1C contains an EDS image and analyses show small particles containing greater amounts of Pd, while the aggregates contain greater amounts of Au. Hence the NCs are heterogeneous. XPS graphs of the Pd/Au (3:1) stabilized by CSPVP (graphs not shown) revealed the binding energy of two maximums at 83.82±0.01 eV and 338.05±0.06 eV deriving from 4f$_{7/2}$ Au and 3d$_{5/2}$ Pd, respectively. A peak at 1.52 Å (1.75 FT magnitude) displays in the EXAFS spectra (graph not shown) suggesting the Pd—O shell due to the coordination of the amide function of CSPVP with Pd. It is hypothesized that the oxygen atom of amide function of chiral pyrrolidinone moiety complexes with Pd and catalytic reactions take place on the electron-enriched Pd(Au) particles, since the 3:1 ratio of Pd/Au nanocluster is more reactive (provided higher chemical yields and greater enantioselectivity) than those of 1:1 ratio of Pd/Au or Au or Pd nanoclusters alone.

The following is a representative experimental procedure for the synthesis of a CSPVP and formation of a Pd/Au—CSPVP complex. First, optically pure (R)-5-benzyl-1-vinyl-2-pyrrolidinone was synthesized as shown below.

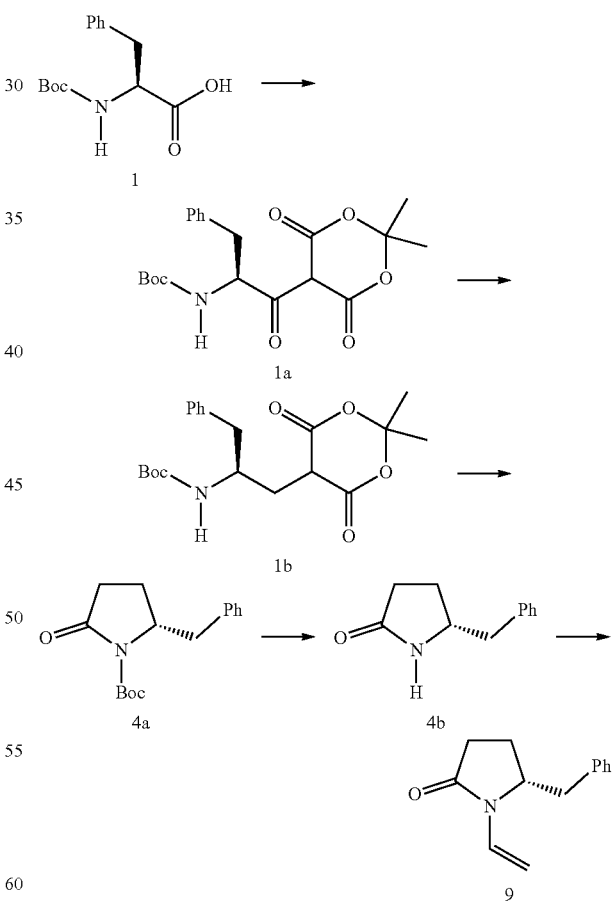

A solution of 0.16 g (0.61 mmol) of Boc-L-phenylalanine, 0.13 g (0.92 mmol) of Meldrum's acid, and 0.11 g (0.92 mmol) of 4-(dimethylamino)pyridine (DMAP) in 8 ml of dichloromethane under argon was cooled to 0° C. over an ice-water bath. To it, a solution of 0.14 g (0.62 mmol) of N,N'-dicyclohexylcarbodiimide (DCC) in 2 ml of dichloromethane was added dropwise. White precipitate (dicyclohexyl urea) appeared, and the mixture was stirred for 12 hours under argon and filtered to remove the byproduct, N,N'-dicyclohexyl urea. The filtrate (containing the product) was washed with 25 ml of 5% HCl and then water, dried under vacuum to give 0.226 g (95% yield) of compound 1a as a white solid. This compound, illustrated above as 1a ((R)-tert-butyl-1-(2,2-dimethyl-4,6-dioxo-1,3-dioxan-5-yl)-1-oxo-3-phenylpropan-2-ylcarbamate) was used in the following step without further purification.

To a cold (0° C.) solution of 0.32 g (0.82 mmol) of compound 1a in 10 ml of dichloromethane under argon were added 0.30 ml (4.9 mmol) of acetic acid and 0.08 g (2.13 mmol) of NaBH$_4$. The solution was stirred at 0° C. for three hours and at 25° C. for 24 hours, diluted with water, and extracted with dichloromethane three times. The combined organic layers were washed with water and brine, dried (anhydrous Na$_2$SO$_4$), concentrated to give a yellow oil, which was crystallized from diethyl ether to give 0.268 g (87% yield) of compound 1b ((R)-tert-butyl 1-(2,2-dimethyl-4,6-dioxo-1,3-dioxan-5-yl)-3-phenylpropan-2-ylcarbamate) as a white solid.

A solution of 0.26 g (0.69 mmol) of compound 1b in 5 ml of toluene under argon was heated to reflux for 6 hours, cooled to 25° C., concentrated over a rotary evaporator and then under vacuum to give 0.18 g (94% yield) of compound 4a ((R)-tert-butyl 5-benzyl-2-oxopyrrolidine-1-carboxylate) as a yellow oil.

A solution of 0.12 g (0.43 mmol) of compound 4a in 10% trifluoroacetic acid (TFA) in dichloromethane was stirred at 25° C. for 30 minutes, diluted with dichloromethane, washed with an aqueous solution of NaHCO$_3$, then water and brine, dried (MgSO$_4$), concentrated to give 0.068 g (88% yield) of compound 4b ((R)-5-benzylpyrrolidin-2-one) as a brown oil. This material was used in the subsequent step without further purification.

To a solution of 0.1 g (0.58 mmol) of compound 4b in 5 ml of vinyl acetate under argon, were added 0.4 g of 3 Å molecular sieves, 6.5 mg (0.02 mmol) of Na$_2$PdCl$_4$, and 0.14 g (1 mmol) of K$_2$CO$_3$. The mixture was stirred at 50° C. under argon for 28 hours, cooled to 25° C., filtered, and concentrated under vacuum, and column chromatographed on silica gel using a mixture of hexane and diethyl ether (1:1) as an eluent to give 0.061 g (52% yield) of pure compound 9 ((R)-5-benzyl-1-vinylpyrrolidin-2-one) as a brown oil.

Next, polymer 14 (scheme 1) was synthesized from compound 9 as shown below.

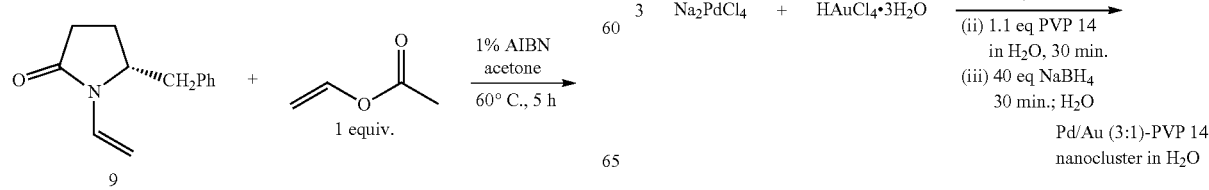

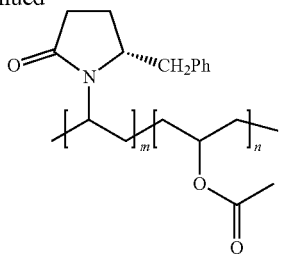

copolymer 13a

79% yield

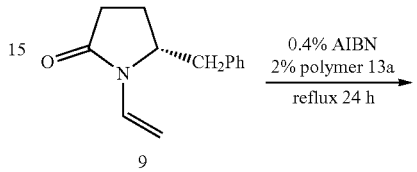

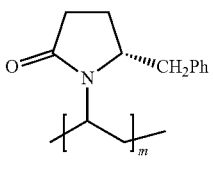

14

71% yield

Molecular weight: 76,000
determined by size exclusion
chromatography (water as solvent)

To a solution of 0.10 g (0.5 mmol) of compound 9 and 0.043 g of vinyl acetate in 0.17 ml of acetone under argon, was added 0.014 g (0.085 mmol) of AIBN, and the solution was stirred under reflux for 10 hours. The solution was cooled to 25° C., poured into hexane, stirred for 10 minutes, and the white precipitate was collected by filtration, dried under vacuum to give 0.112 g (79% yield) of copolymer 13a as a white solid.

To a hot (60° C.) solution of 0.003 g of copolymer 13a in 0.6 ml ethyl acetate under argon, were added 0.3 g (1.49 mmol) of compound 9 and 0.001 g of AIBN. The solution was stirred for 24 hours, cooled to 25° C. and poured into hexane. The precipitate was collected by filtration, dried under vacuum to give 0.213 g (71% yield) of polymer 14 as a white solid. Chiral PVP 14 (poly-(R)-5-benzyl-1-vinylpyrrolidinone) having molecular weight of 76,000 was achieved and this polymer was used in the nanocluster preparation. The molecular weight was determined by gel permeation chromatography using TSKgel GMHx1 column and water as solvent with a flow rate of 1 mL/min.

Next, compound 14 was used in the preparation of Pd/Au—CSPVP nanoclusters in a water solution according to the below.

3 Na$_2$PdCl$_4$ + HAuCl$_4$·3H$_2$O  →  (i) H$_2$O  0° C., 20 min.  (ii) 1.1 eq PVP 14 in H$_2$O, 30 min.  (iii) 40 eq NaBH$_4$  30 min.; H$_2$O Pd/Au (3:1)-PVP 14 nanocluster in H$_2$O A 188 µL of 10 mmol/L of $Na_2PdCl_4$ in deionized water solution and 62 µL of 10 mmol/L of $HAuCl_4·3H_2O$ in deionized water solution were added into 2 ml of deionized $H_2O$. The solution was cooled to 0° C. over an ice-water bath, stirred for 20 minutes, and added 0.5 mL of a 1.39 mmol/L of chiral PVP 14 solution, and stirred for 30 minutes. To it, was added a solution of 0.25 ml of 0.1 mol/L of $NaBH_4$ in water. The color of the solution changed to black and stirred for 30 minutes at 25° C. to give the Pd/Au (3:1)-PVP 14 nanoclusters in aqueous solution. This solution was used for various oxidation reactions. As noted above, the CSPVP molecules can also interact with biomolecules such as proteins, DNA, and RNA (e.g., siRNA and dsRNA). Chiral recognition using chiral PVP can be achieved from the interaction with the biomolecule, thereby allowing either selective isolation or detection of specific biomolecules. Hence the present invention can be used in separation, detection, and nanodelivery of biomolecules.

A polymer of α-hydroxy-N-vinyl-pyrrolidinone was synthesized from the polymerization of α-acetoxy-N-vinylpyrrolidinone and copolymer of α-hydroxy-N-pyrrolidinone and vinyl acetate as shown in Scheme 2. The synthetic sequence involved α-hydroxylation of N-vinylpyrrolidinone (a commercially available material) with lithium diisopropylamide (LDA) in THF at −78° C. followed by $MoO_5$(pyridine)(HMPA) complex. α-Hydroxy-N-vinylpyrrolidinone was acetylated with acetic anhydride ($Ac_2O$) and pyridine followed by copolymerization with vinyl acetate and a catalytic amount of AIBN in refluxing acetone to give the copolymer. This copolymer was used as a catalyst for the polymerization of α-hydroxy-N-vinylpyrrolidinone to give α-hydroxy-PVP after removal of the acetoxy protecting group with potassium carbonate in methanol. The molecular weight of α-hydroxy-PVP was determine to be 67,425 Da. Notably, chiral α-hydroxy-PVP containing a stereogenic center at the alpha-carbon of the amide carbonyl function can be synthesized using chiral oxaziridine reagent instead of $MoO_5$(pyridine)(HMPA).

Scheme 2
Synthesis of α-hydroxy PVP.

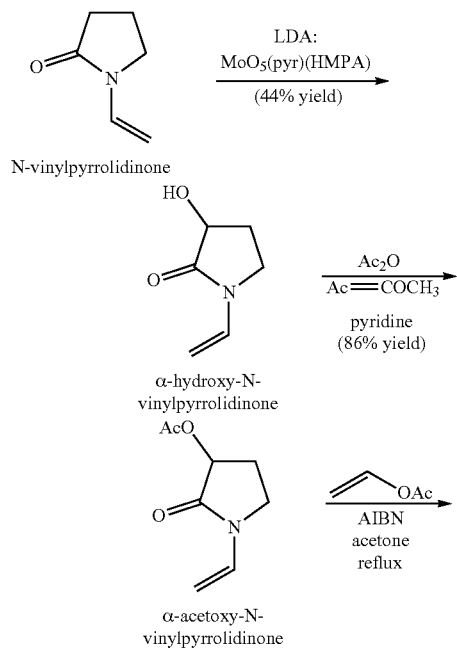

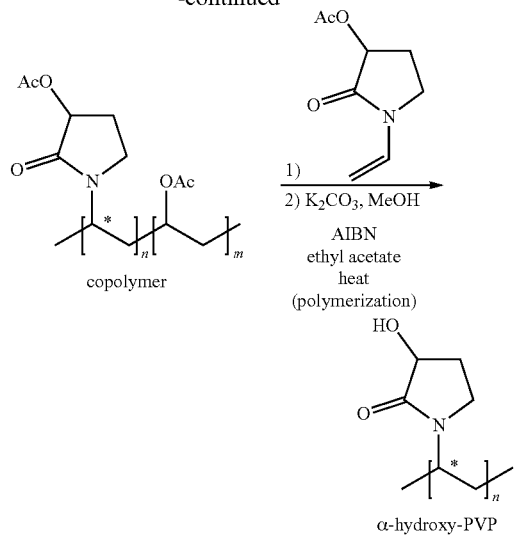

Figure 3:
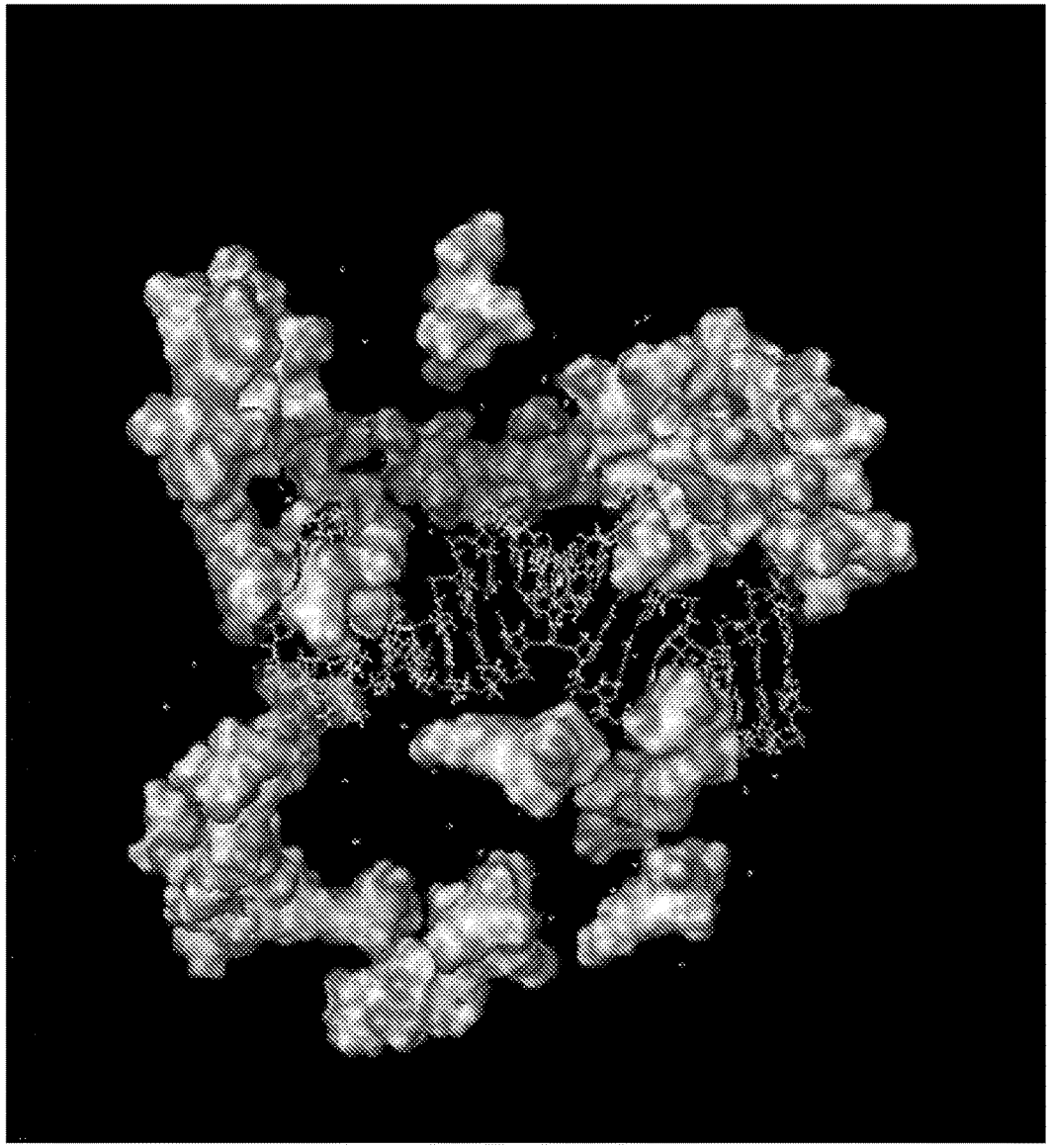
FIG. 3 is a model illustrating the results of a computational simulation of α-hydroxy PVP (shown in surface structure) and siRNA (shown in ball-and-stick structure)

In simulation of this concept with α-hydroxy PVP, it was found that there are at least two clear hydrogen bonds between the OH group of α-hydroxy PVP and the phosphate backbone of the siRNA. FIG. 2 illustrates one of the hydrogen bondings between α-hydroxy-PVP and siRNA. FIG. 3 illustrates the results of the computational simulation of α-hydroxy-PVP and siRNA. The siRNA molecule is shown in ball-and-stick mode and α-hydroxy-PVP is shown in surface structure. The simulation results support that α-hydroxy-PVP can encapsulate siRNA effectively.

In order to test this concept, encapsulation of a 523 base-pair double-strained DNA (dsDNA; MW 509,402) (5% by weight) was carried out by mixing with α-hydroxy-PVP in deionized water for 10 minutes at room temperature. The resulting solution was lyophilized to give a white powder. FIG. 4A is an AFM image of the initial α-hydroxy-PVP and FIG. 4B is an AFM image of the encapsulated α-hydroxy-PVP/dsDNA support the encapsulation in which the original α-hydroxy-PVP showing a spherical material with diameter of ~90 nm. After encapsulation, the materials showed a uniformed elongated materials with a length of ~250 nm and width of 40 nm. The change of shapes from spherical to elongated materials imply that the polymer α-hydroxy-PVP is wrapping around dsDNA. The estimated length of 523 base-pair dsDNA is 157 nm.

Figure 5:
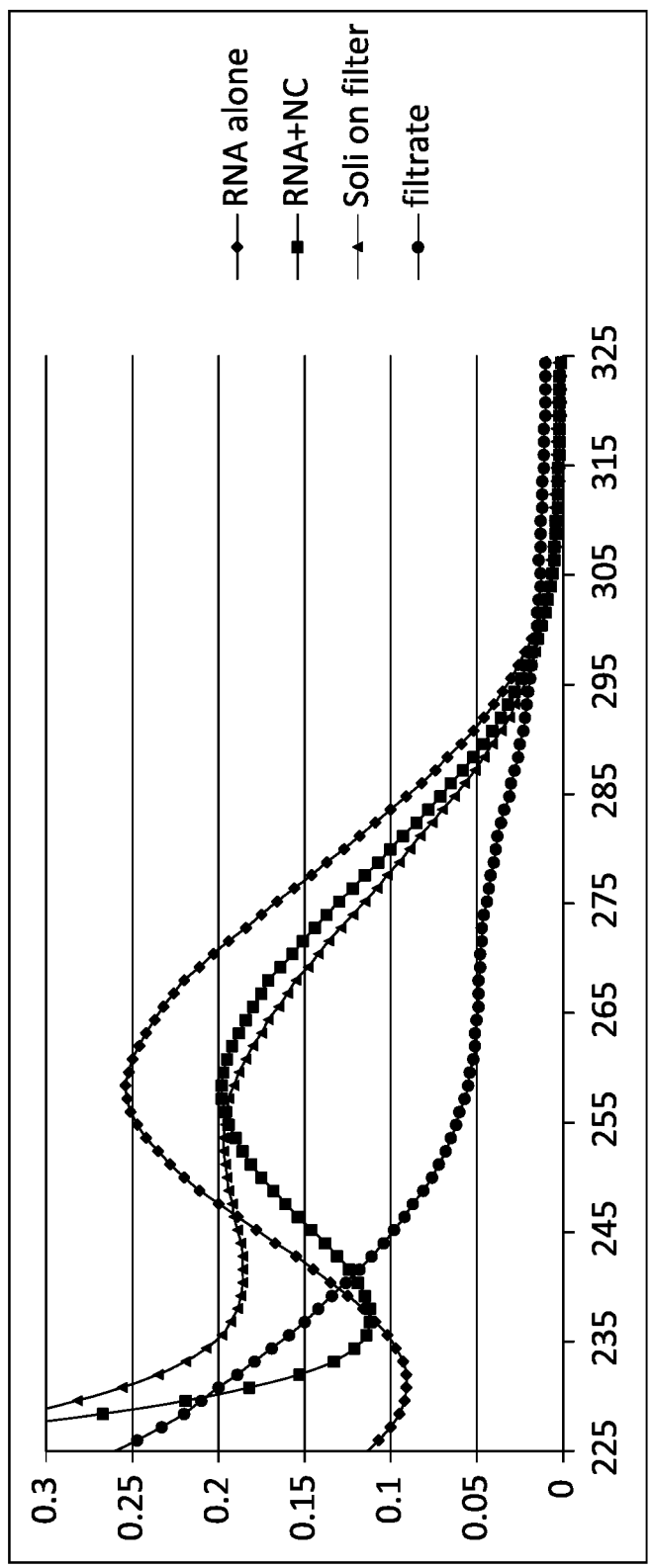
FIG. 5 is UV/vis spectra of siRNA (18 mers) alone, encapsulated α-hydroxy-PVP/siRNA, solid material after centrifugative filtration, and the filtrate.

Encapsulation of 18-mer siRNA (MW by α-hydroxy-PVP was also carried out by following a similar protocol as described above. The resulting aqueous solution was filtered through a membrane equipped with a 10,000 MW cutoff to remove any unbound siRNA. The solid was collected, dissolved in deionized water, and lyophilized to give a white powder (~100% yield based on the weight). The UV/vis spectra shown in FIG. 5 support the encapsulation in which the polymer (nanocarrier)-siRNA shows a reduction of UV absorbance comparing with the original siRNA. AFM imaging was also used to study the encapsulation and the images showed the encapsulated materials are spherical materials with a diameter of ~160 nm.

As illustrated in the following Scheme 3, self-assembly of α-hydroxy-PVP to form micelle structure can be accomplished by incorporation of RNA-interacting and cell penetrating peptide fragment (such as peptide 12) and hydrophobic alkyl group (such as 13). This polymer, 14, likely forms micelle with the alkyl group orients in the internal core and the polar hydroxyl group and peptide chain in the peripheral site. The peptide chain can selectively bind to RNA due to the peptide sequence and positively charged amino acid residues such as lysine residues.

Scheme 3
Synthesis of substituted PVP derived nanocarriers.

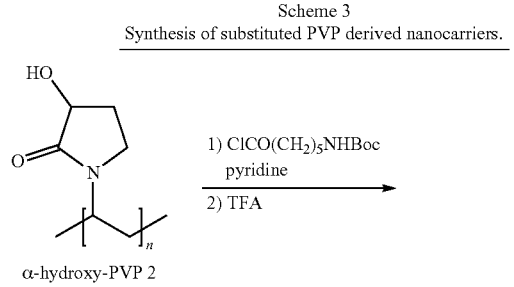

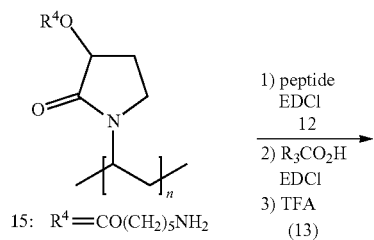

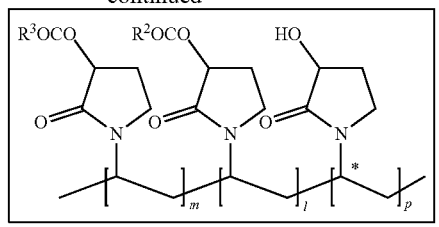

14: $R^2$=(CH$_2$)$_5$NH—GKLKLLKKW;

$R^3$=(CH$_2$)$_5$NH—CO(CH$_2$)$_{16}$CH$_3$

Peptide 12: Boc—WKKLLKLKG—OH; R$_3$CO$_2$H=CH$_3$(CH$_2$)$_{16}$CO$_2$H

The CSPVP/nanocluster complexes can be used to catalyze a wide variety of asymmetric oxidation reactions used in enantioselective synthesis of various chiral molecules useful in the synthesis of, for example, chiral drugs. In these reactions, a mixture of two mirror image molecules (two enantiomers) is reacted with oxygen and potassium carbonate reagents in the presence of the CSPVP-Pd/Au nanocluster complex. However, it is also within the scope of the present invention to perform other reduction reactions including ketones, alkenes, alkynes, and imines, such as through the use of hydrogen gas instead of oxygen.

Chiral syn- and anti-1,2-diols are common functional groups in natural products and are important intermediates in the chemical and pharmaceutical industry. Catalytic amounts of CSPVP and environmentally friendly metals such as gold and palladium (low toxicity) can be used in enantioselective oxidation processes.

Utilizing a combination of bimetallic nanoclusters and CSPVPs, several enantioselective oxidation reactions of cycloalkanediols and cycloalkanes, and oxidative C—C bond forming reactions (using PVP) were investigated. Scheme 4, below, depicts exemplary working models and un-optimized results of the catalytic diol oxidation reactions.

Scheme 4.
Working models and results of the oxidation reactions.

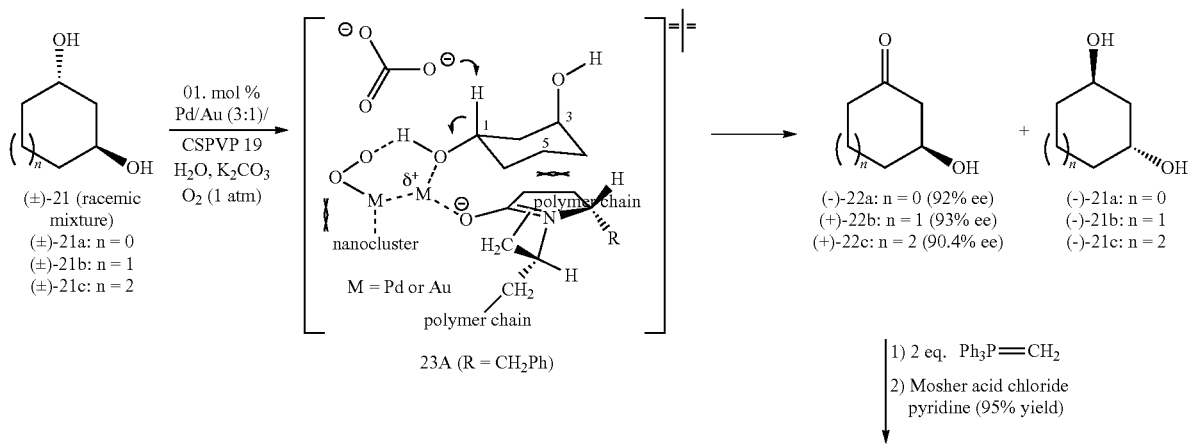

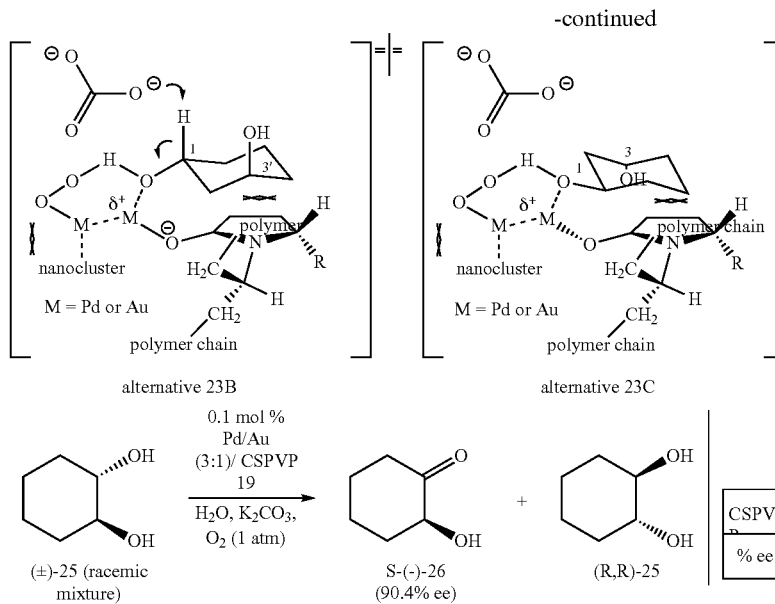

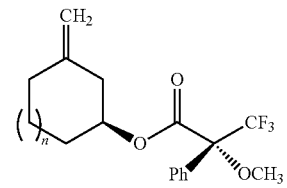

24a: n = 0
24b: n = 1
24c: n = 2

Table 1. % ee of (+)-22b from the oxidation of (±)-21b.

| CSPVP | 18 | 15 | 14 | 16 | 17 | 19 |
|---|---|---|---|---|---|---|
| % ee | 70 | 83 | 88 | 91 | 91 | 92 |

Oxidation of alcohols often results in the loss of a stereogenic center (carbon possessing the OH group). In this example, a challenging oxidative kinetic resolution of a racemic mixture (1:1) of (±)-cycloalkanediols such as compounds (±)-21a-(±)-21c was studied. Excellent enantioselectivities were found from aerobic oxidation reactions of (±)-21a-(±)-21c with 0.1 mol % of Pd/Au (3:1)/CSPVP and $O_2$—$K_2CO_3$ in water at 50-60° C. (Scheme 2). For instance, using CSPVP 19 (Scheme 1), a 93% ee of (S)-(+)-3-hydroxycyclohexanone (22b) [47% chemical yield; or 94% yield based on (+)-21b] along with 50% of recovered (−)-21b were isolated after silica gel column chromatography. No 1,3-cyclohexanedione was found. The specific rotation $[\alpha]_D^{23}$ of 22b is +42.3 (c 0.80, $CHCl_3$) and the reported optical purity of S-3-hydroxycyclohexanone having specific rotation of +37.3 (c 0.80, $CHCl_3$) is 82% ee. The optical purity of (+)-22b was determined by converting it to Mosher ester 24b, and its $^1H$ NMR spectrum reveals the optical purity. In the NMR spectrum of 24b, the two diastereomers show different chemical shifts for the =$CH_2$ and methoxy protons. The =$CH_2$ signals of major isomer appear at δ 4.78 and 4.73 ppm (singlets) and the minor isomer at δ 4.73 and 4.67 ppm (singlets), and the OMe signals of major isomer at δ 3.56 and minor isomer at δ 3.54 ppm. Different CSPVPs were used in the oxidation of (±)-21b, and results are summarized in Table 1 (embedded inside Scheme 4) in which polymer 19 provided the highest enantioselectivity. Oxidation of cyclopentanediol (±)-21a using CSPVP 19 gave (−)-22a having $[\alpha]_D^{23}$=−31.8 (c 0.56, $CH_2Cl_2$; S configuration, 92% ee) (the literature notes $[\alpha]_D^{23}$=+28.7 (c 0.57, $CH_2Cl_2$), 83% ee for R-configuration). Similarly, using CSPVP 19, the optical yield of (+)-22c is 90.4% ee having $[\alpha]_D^{22}$=+15.5 (c 0.8, $CHCl_3$). The % ee's of (−)-22a and (+)-22c were determined from the $^1H$ NMR spectra of Mosher derivatives 24a and 24c (similar to 24b, the olefinic and methoxy protons of the diastereomers show different chemical shifts). Optically enriched diols (−)-21a, (−)-21b and (−)-21c were recovered in the oxidation reactions (50-54% yields). The results suggest (S,S)-diols react faster than the (R,R)-diols under the chiral supported bimetallic nanocluster environment (kinetic resolution) and bulkier R' of CSPVPs provides greater % ee (Table 1). Based on these results, it is believed that transition state (TS) 23A (Scheme 4) has the lowest energy in the oxidation of 21b (a representative diol), in which the amide of the polymer and equatorial (C1) hydroxyl oxygen of 21b complexes with Pd (likely) or Au, where C3-OH positions away from the polymer chain and opposite to C5-R group. Subsequent removal of C1-H by $K_2CO_3$ leads to (+)-22b. The Pd/Au nanocluster likely hinders the cyclohexane ring of 21b to approach the active site from the opposite side of the lactam ring. If 21b approaches the active site from different directions with similar energies, there will likely be no enantioselectivity observed, which is not what has been observed. The C3'-OH of alternative TS 23B positions closer to the polymer chain resulting in a higher energy structure (repulsion). TS 23C possesses the highest energy due to steric repulsion resulted from the C3- or C3'-OH with the lactam ring.

Figure 6:
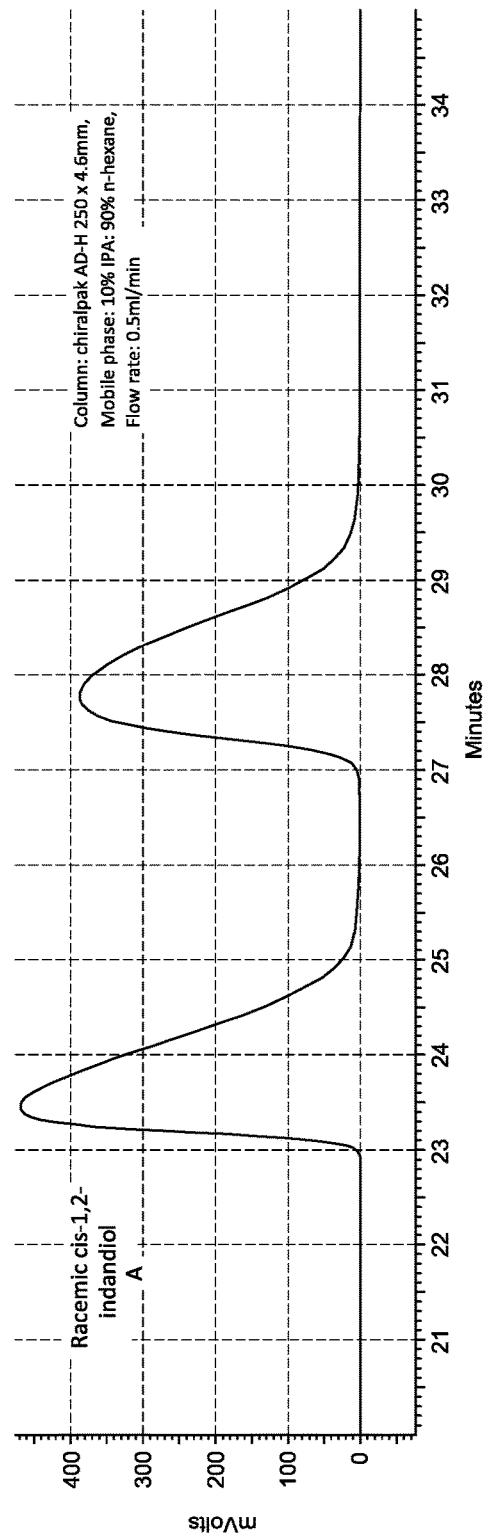
FIG. 6 is an HPLC graph of the dibenzoate derivative of (−)-21b.
Figure 6:
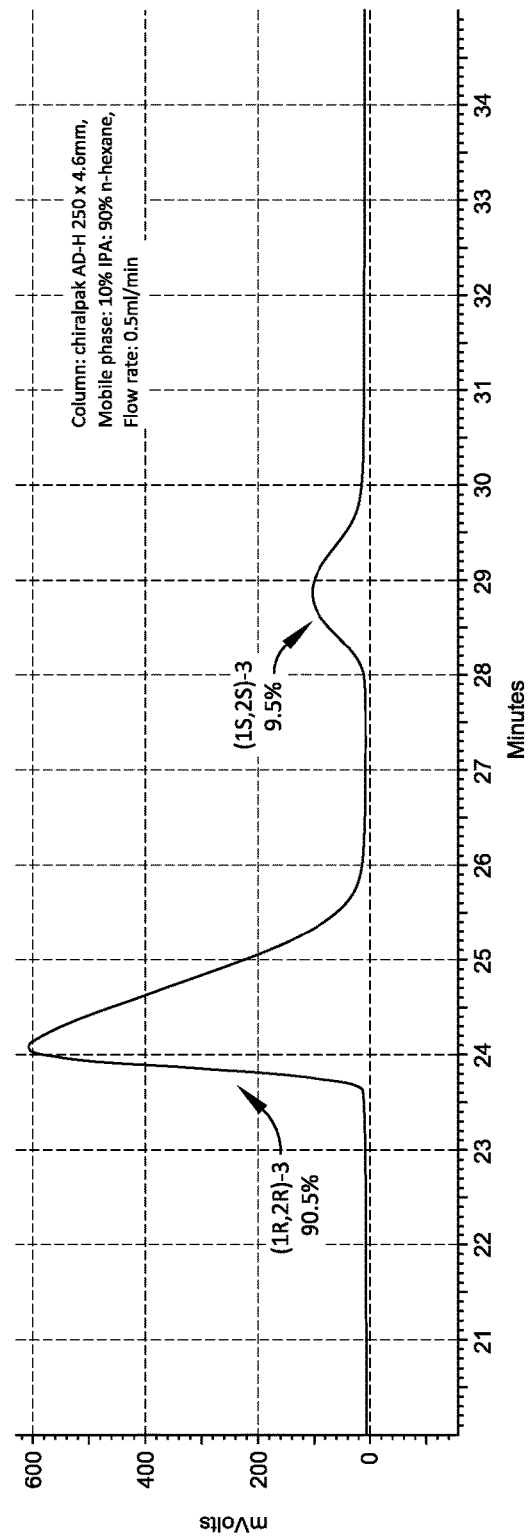

Recovered diols (−)-21a-(−)-21c can be re-treated with Pd/Au (3:1)/CSPVP 19 or 16 to obtain greater optically enriched (−)-21a-(−)-21c. For instance, after oxidation with Pd/Au (3:1)/19, specific rotation of (−)-21b is $[\alpha]_D^{25}$=−3.14 (c 1.0, $CHCl_3$) and optical purity is 91% ee (literature reports +3.0 c 1.0, $CHCl_3$; for 87% ee; 1S,3S-configuration). The % ee of (−)-21b obtained from Pd/Au (3:1)/16 (the specific rotation shows it to be 89% ee) was determined through its dibenzoate derivative (from the treatment of (−)-21b with benzoyl chloride and pyridine) by HPLC using Chiralpak AD(-H) column (FIG. 6). The catalysts appear to be stable. Hence, the IR and NMR spectra of the recovered CSPVP 14 (after purification by column chromatography using Amberlite IR-120 gel) are similar to that of the authentic sample. Moreover, CSPVP 18, which contains a hydroxyl function, was used in the oxidation of (±)-21b, and product (+)-22b was isolated in 48% yield (70% ee). After quenching the reaction with water and extraction with $CH_2Cl2$, the aqueous layer was concentrated and subjected onto an ion exchange (Amberlite IR-120) column (eluted with water and methanol) to recover CSPVP 18, whose IR and NMR spectra are identical to that of authentic 18 suggesting no oxidation of the hydroxyl group took place.

Oxidation of 1,2-diol (±)-25, under similar reaction conditions using CSPVP 19, provided (S)-(−)-26 in 90.4% ee {based on $[\alpha]_D^{23}=-18.8$ (c 0.65, CHCl$_3$); literature discloses +20.8, c 0.65, CHCl$_3$; 100% ee, R-configuration}. When CSPVP 14 was used, only 83% ee of (−)-26 (45% yield) was found along with 47% yield of (R,R)-25 ($[\alpha]_D^{23}=-17.1$ (c 1.6, H$_2$O; 37% ee), suggesting that the stereoselectivities likely are affected by the steric bulkiness of C5-substituent R' of CSPVPs. It was found that 2-cyclohexenol undergoes oxidation with Pd/Au (3:1)/CSPVP/O$_2$ at 25° C. in a few hours to give 2-cyclohexenone implying the allylic hydroxyl function oxidizes faster than the OH of cycloalkanediols. No oxidation of the alkene function takes place. When 0.1 mol % of Pd or Au nanoclusters alone (diameters of the nanoclusters are ~3.0 nm) were used, the chemical and optical yields of the aforementioned oxidation reactions are lower than those using Pd/Au (3:1) (data not shown).

Other diols can undergo enantioselective oxidation, such as meso-cis-1,3 diols 51-56a, 58a, and (±)-57a, as shown in Scheme 5. Alcohols are oxidized using O$_2$ and K$_2$CO$_3$ as the oxidant and the products are depicted in 22a-22e and 52b-58b. Diol (±)-57a and meso-58a are made from (±)-59, which was derived from allylamine and butadiene monoxide followed by protection with Boc$_2$O, and ring closing with the Grubbs' catalyst. Compound 58a is made from the oxidation of 59 with OsO$_4$-NMO (N-methyl-morpholine-N-oxide. Compound (±)-57a is made from the hydroxyl directed hydromercuration of 59 followed by reduction with NaBH$_4$. The presence of the carbamate function in 57a and 58a should not affect the alcohol oxidation reactions. It is believed that oxidation of triol 58a will result in selective oxidation of only the C3-OH, a first example of enantioselective oxidation of contiguous triols. The products and recovered optically active 57a can serve as key synthetic intermediates leading to various glycosidase inhibitors iminosugars, potential drugs for the treatment of carbohydrate-induced diseases.

In still another embodiment, aryl alkyl carbinols, such as (±)-60 can be accomplished. It is believed that (S)-60 can be oxidized using CSPVP 19 (or other CSPVPs), and (R)-60 will be recovered.

Scheme 5.
Oxidation of alcohols.

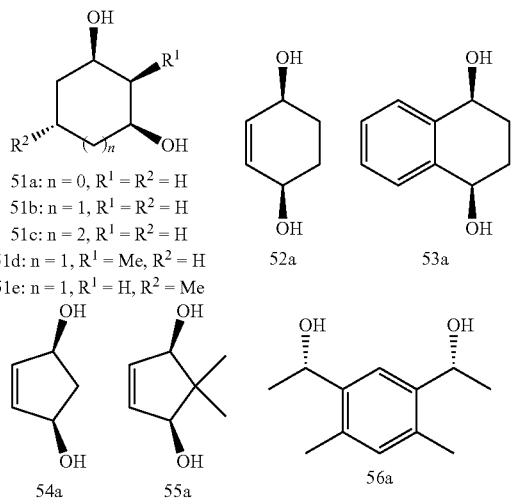

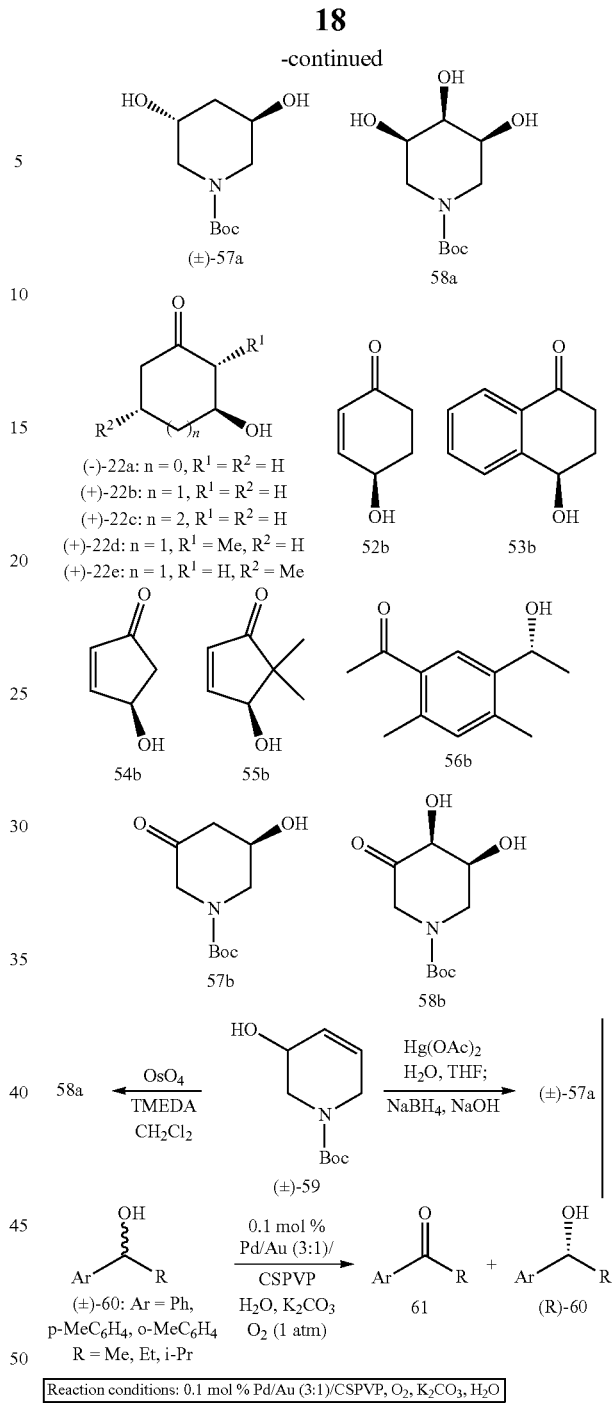

Regio- and enantio-selective C—H oxidation of alkanes and cycloalkanes is one of the most challenging transformations in organic synthesis. A few cyclohexane substrates, bimetallic nanoclusters, chiral stabilizers, and oxidants were surveyed. It was found that, in certain embodiments of the present invention: (1) for C—H oxidation, Cu/Au (3:1)/CSPVP provided better results than those of Pd/Au (3:1)/CSPVP and Fe/Au (3:1)/CSPVP, and H$_2$O$_2$ (in place of O$_2$ and K$_2$CO$_3$) was needed for the oxidation; (2) in general, the rate of oxidation of alcohols is faster than that of alkanes; (3) methylene (CH$_2$) moiety oxidizes much faster than methine (CH) and methyl (CH$_3$) groups; (4) sterically unhindered or rotationally restricted CH$_2$ selectively oxidizes in the presence of hindered or rotationally unrestricted ones; and (5)

alkenes (including allylic CH$_2$) do not undergo appreciable reactions under the OH or C—H oxidation reaction conditions. These un-optimized results are summarized in Scheme 6, below.

Scheme 6.
Working models and results of C-H oxidation reactions.

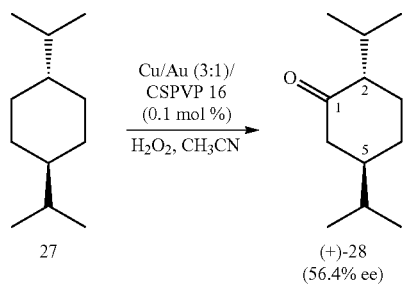

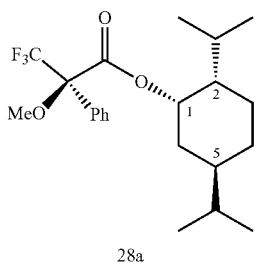

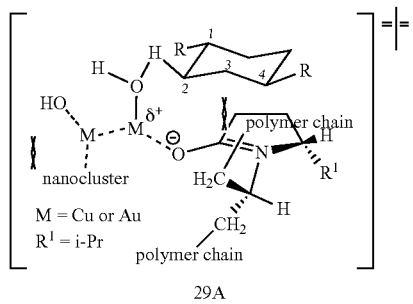

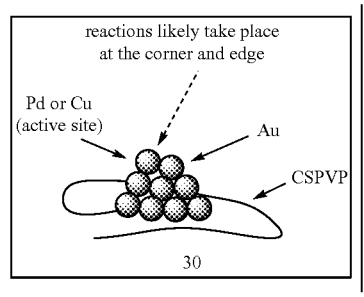

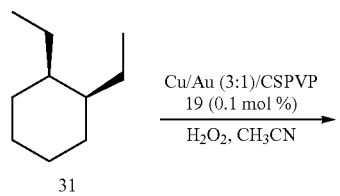

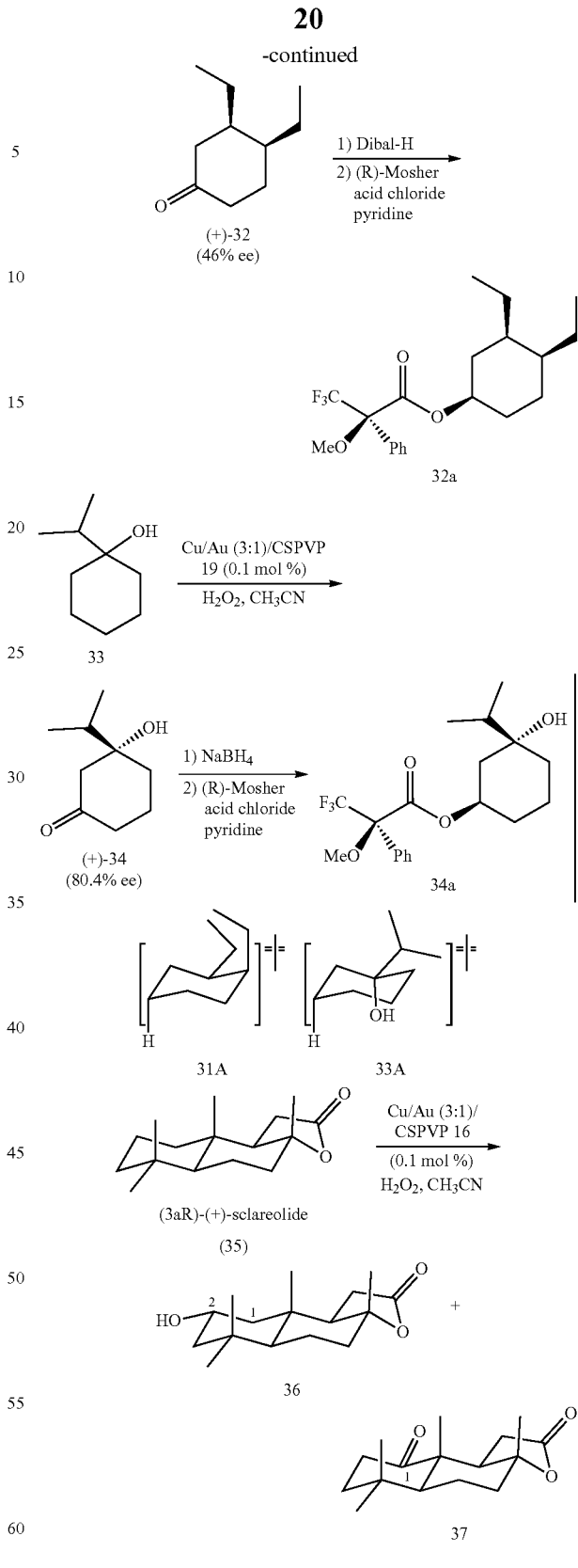

Oxidation of trans-1,4-diisopropyl-cyclohexane (27) with Cu/Au (3:1)/CSPVP 16 (0.1 mol %) and H$_2$O$_2$ in aqueous acetonitrile at 50° C. gave an 84% chemical yield (based on recovered 27) and 56.4% ee of (2S,5R)-(+)-28 ([α]=+8.8, c 0.25, CHCl$_3$). The absolute configuration was assumed based on the specific rotation of (2R,5R)-(+)-2,5-dimethyl-cyclohexanone. The % ee was determined from the ¹H NMR spectral data of Mosher derivative 28a, which was obtained from the reduction of 28 with Dibal-H followed by (R)-Mosher acid chloride. In the ¹H NMR spectrum, the methoxy signal of major diastereomer of 28a appears at δ 3.57 ppm and the minor isomer at 3.55 ppm. Remarkably, no other regioisomers were detected from the oxidation reaction. The hypothetical working model for this reaction is illustrated in structure 29A in which the Cu (of the Cu/Au nanoclusters) complexes with the peroxide. The C1 & C4 R groups orient at the equatorial positions. This model leads to the major enantiomer, and the mirror image of the cyclohexane moiety provides the minor enantiomer. Abstraction of the equatorial (or axial) C2-H of 27 followed by either combination with •OH or abstraction of HO• from $H_2O_2$ from the resulting radical gives the corresponding alcohol, which oxidizes to 28. It is believed that the nanoclusters of Cu/Au block one side of 29A and the polymer chain repulses C1-R group (if orients at C3) of the cyclohexane ring leading to a lower energy TS conformer, 29A. To study the stability of the CSPVP under the oxidation reaction conditions, the recovered CSPVP was analyzed. For example, after the C—H oxidation reaction, the CSPVP 14 was recovered by subjecting the lyophilized aqueous layer onto an ion exchange resin (Amberlite IR-120) column, and the fractions containing the polymer were concentrated. The IR and NMR spectra of the recovered polymer were similar to those of the authentic polymer 14 suggesting no oxidation of the lactam ring or alkane backbone took place. It is believed that the CSPVP wraps around the bimetallic nanoclusters, and a number of Cu/Au atoms are exposed to the outside, which undergo oxidation reaction (see 30, Scheme 5). The oxidation does not affect the polymer. It is further believed that the use of bulkier R' group in CSPVP will increase the enantioselectivity.

Oxidation of 1,2-cis-diethylcyclohexane (31) using Cu/Au (3:1)/19 and $H_2O_2$ gave (+)-32 {$[\alpha]_D^{25}$=+17.0 (c 0.1, $CHCl_3$)} in 75% yield based on recovered starting 31 (43% recovery) and in 46% ee. The % ee was determined from the ¹H NMR spectrum of Mosher derivative 32a, which was obtained from the reduction of (+)-32 with Dibal-H followed by (R)-Mosher acid chloride and pyridine. In the ¹H NMR spectrum, the methoxy signal of major diastereomer of 32a appears at δ 3.56 ppm and the minor isomer at 3.55 ppm. The absolute configuration was assumed based on the reported specific rotation of (3R,4S)-3,4-dimethyl-cyclohexanone. No 2,3-cis-diethylcyclohexan-1-one and other regioisomers (such as oxidation of the methine or ethyl functions) were found suggesting steric effect, rotational restriction around C—C bond, and bond strengths control the regioselectivity. Conformer 31A is hypothesized to enter the reaction active site. Due to the symmetry of molecule 31, C—H oxidations take place at C4 and C5 of 31.

A possible hydroxyl-directed oxidation was found when 33 was treated with 0.1 mol % Cu/Au (3:1)/19, only (+)-34 [76% yield based on recovered 33; $[\alpha]_D^{25}$=+5.3 (c 0.2, $CHCl_3$)] was obtained in 80.4% ee based on the ¹H NMR spectrum of Mosher derivative 34a, which was obtained from the reduction of 34 with $NaBH_4$ followed by (R)-Mosher acid chloride. In the ¹H NMR spectrum of Mosher derivative 34a (only the secondary alcohol reacted with Mosher acid chloride), the methyl signal (doublet) of the isopropyl moiety of the major diastereomer appears at δ 1.00 ppm and that of the minor isomer at δ 1.09 ppm, and the methoxy singlet signals at δ 3.56 and 3.55 ppm, respectively for the major and minor isomer. In the reduction of (+)-34 with $NaBH_4$, only (1R,3R)-1-i-propyl-1,3-cyclohexanediol was found, and the C3 stereochemistry of this diol is assigned base on the J values of C3-H (axial oriented H; appears at δ 3.81 ppm as a triplet of triplet) showing 8.4 (axial, axial coupling) and 4.8 Hz (axial, equatorial coupling) in the ¹H NMR spectrum. The structure of (+)-34 was identified by its NMR and MS spectra along with those of 34a and 34a's diol precursor. No 4-hydroxy-4-isopropylcyclohexanone and 2-hydroxy-2-methyl-cyclohexanone (likely due to steric repulsion) were found from the oxidation reaction implying the hydroxyl group may direct the oxidation. It is believed that conformation 33A approaches the nanoclusters.

A common drawback of C—H oxidation using conventional nanoparticle catalysts is that only oxidation of small-sized organic molecules can be performed. However, C—H oxidation of a more complex molecule using the nanocluster catalysts of the present invention has been examined. (+)-sclareolide (35), a medium-sized molecule, was oxidized under mild reaction conditions and provided a high degree of regioselectivity. In an oxidation reaction of (+)-sclareolide (35) with 0.1 mol % Cu/Au (3:1)/16 and $H_2O_2$, alcohol 36 (likely equatorial based on the J values of C2-H signal of 36 in ¹H NMR spectrum) and ketone 37 were isolated as the major products in a ratio of 2:1 along with small amounts of C2-ketone of 36 and C3-ketone. The C2-ketone is likely derived from the oxidation of alcohol 36. The results suggest steric and electronic effects appear to be the governing factors for the regioselectivity of the oxidation reactions, and CH and $CH_3$ groups and $CH_2$ adjacent to electron-withdrawing function do not undergo (or in lower reaction rates) oxidation.

To examine the regioselectivity further and explore the generality and applicability of the oxidation of medium-sized molecules, a class of natural and unnatural products, which are either available from commercial sources or can be synthesized in a laboratory, can be oxidized as shown in Scheme 7, below.

Scheme 7. C-H oxidations of medium-sized molecules.

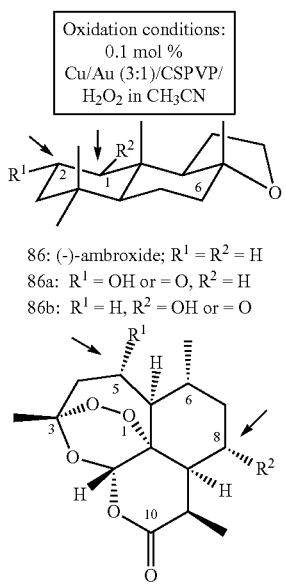

86: (-)-ambroxide; $R^1 = R^2 = H$
86a: $R^1$ = OH or = O, $R^2 = H$
86b: $R^1 = H$, $R^2$ = OH or = O 87: (+)-artemisinin;
$R^1 = R^2 = H$
87a: $R^1$: = O, $R^2 = H$
87b: $R^1 = H$, $R^2$: = O

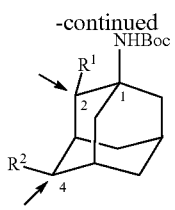

88: N-Boc-1-aminoadamantane;
R¹ = R² = H
88a: R¹: =O, R² = H
88b: R¹ = H, R²: =O

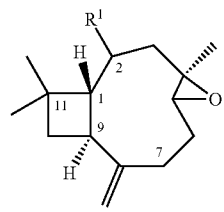

89: (−)-carophyllene oxide;
R¹ = H
89a: R¹: =O

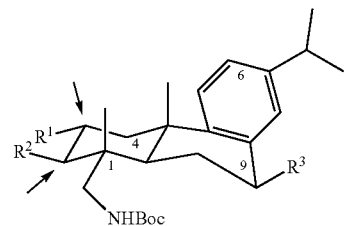

90: N-Boc-dehydroabietylamine;
R¹ = R² = R³ = H
90a: R¹: =O, R² = R³ = H
90b: R¹ = H, R²: =O, R³ = H
90c: R¹ = H, R² = H, R³: =O

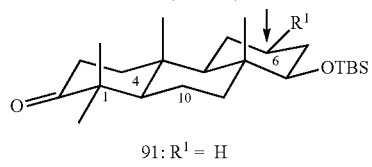

91: R¹ = H
91a: R¹: =O (−)-Ambroxide (86), (+)-artemisinin (87), 1-aminoadamantane (precursor of 88), (−)-caryophyllene oxide (89), and dehydroabietylamine (reaction of this amine with Boc$_2$O will give 90 are available commercially (Sigma-Aldrich). Optically pure 91 can be prepared in a laboratory. Since these compounds, except 88 (achiral), are enantiopure, PVP and different CSPVPs are used separately in the Cu/Au (3:1)/H$_2$O$_2$ catalyzed C—H oxidation reactions to examine the regioselectivity. The results of the oxidation of these compounds provides not only the regioselectivity but also the stability and effects of functional groups such as cyclic ether (86), peroxide within the 1,2,4-trioxane system (87), rigid molecule (88; enantioselectivity will result), possible direction of NH-Boc group (88 & 90), C=C double bond, epoxide (89), aromatic ring (90), and ketone (91).

The expected oxidation sites are indicated in those carbons next to the arrows as depicted in Scheme 7. Due to the examination of oxidation of various small molecules that do not undergo oxidation under the Cu/Au (3:1)/CSPVP/H$_2$O$_2$ reaction conditions suggesting oxygen decreases the rate of oxidation of the α-carbon and the C=C does not undergo oxidation, it is expected that 86 will undergo oxidation at C2 (major product) and/or C1 (minor) giving 86a and 86b. As shown in the oxidation of sclareolide (see Scheme 7), C5 and C6 of 86 likely oxidize very slowly. It is believed that Artemisinin, an antimalarial drug from plant *Artemisia annua*, undergoes oxidation at C8 (major) or/and C5 (minor) (87a or/and 87b). It is believed that compound 88, a N-Bo protected amantadine (an anti-Parkinsonian agent), undergoes oxidation at C2 (N—H directed oxidation) or/and C4 (88b). C—H oxidation at C2 provides optically active ketone 88a. In compound 89, it is believed that oxidation at C2 takes place to produce 89a, because C2 is the least sterically hindered CH$_2$. The allylic C7-CH$_2$ should not undergo oxidation since it has been discovered that cyclohexene does not oxidize under the reaction conditions. It is believed that compound 90, a N-Boc protected leelamine (an intracellular cholesterol transport inhibitor), undergoes oxidation at C2 and C3 (90a & 90b). The C3-CH$_2$ is the least hindered methylene group, and similar to the discussion of oxidation of 88, there is a possible directing effect from N—H. Oxidation at C9 (benzylic CH$_2$) of 90 may not take place since the aromatic ring, like alkene, may reduce the rate of oxidation reaction. It is believed that tricyclic terpene 91 oxidizes at C6 (major product, 91a). The aforementioned positions of oxidation should not be viewed as limiting, and it is possible that other position(s) could be oxidized. Also depending on the steric effect of the molecules, alcohol products may be produced.

The enantioselective C—H oxidation demonstrated above can be applied to a number of other cycloalkanes and alkanes as depicted in Scheme 8, below. Based on a similar TS as that depicted in 29A (Scheme 6), oxidation of cis-1, 2-disubstituted cyclohexanes 62 using Cu/Au (3:1)/CSPVP/ H$_2$O$_2$ in CH$_3$CN is expected to give ketone 69, and the cyclohexane conformation entering the active site is depicted in 62A (by replacing the cyclohexane ring in 29A with 62A). Also, it is believed that increasing the size of the R group enhances enantioselectivity. Similarly, oxidation of compounds 63-67 produces chiral ketones 70-74, respectively, and the respective conformations are described in 63A-67A. Tetrahydropyrans 68 provide products 75 based on a similar conformation as 65A (the N-Boc group of 65A replaces by oxygen). The electron-negative oxygen likely decreases the rate of oxidation of the adjacent CH$_2$ (C2 & C6 of 68). Compound 65e (R=CN) is available from VWR Int. NJ); 65d (R=OMe), 66a&b, 67, and 68 are available from Sigma-Aldrich, St. Louis, Mo.; 66c and 67a are available from Aurora Fine Chem. San Diego, Calif.; 67b and 67c are available from Aldlab Chem. LLD, Woburn. Mass.; 68a (R=Me) is available from American Custom Chemicals Co., San Diego, Calif.; and 68e (R =CN) is available from Oakwood Chem. West Columbia, S.C.]. Compounds 62 and 64 can be made from the Birch reduction of the corresponding disubstituted benzenes followed by H$_2$/Pd—C, and the resulting cis- and trans-isomers can be separated by column chromatography (as used in the preparation of compounds 27 and 31). Preparations of the dimethyl analog of 63, 4-substituted piperidines 65, 68d (R=OMe) have been reported in the literature. Compounds 68b and 68e (R=Et and i-Pr) can be made from the cyclization of 1-bromo-5-methoxy-3-ethylpentane and 1-bromo-5-methoxy-3-i-propylpentane, respectively with AlCl$_3$.

Scheme 8. Oxidation of cycloalkanes and alkanes.

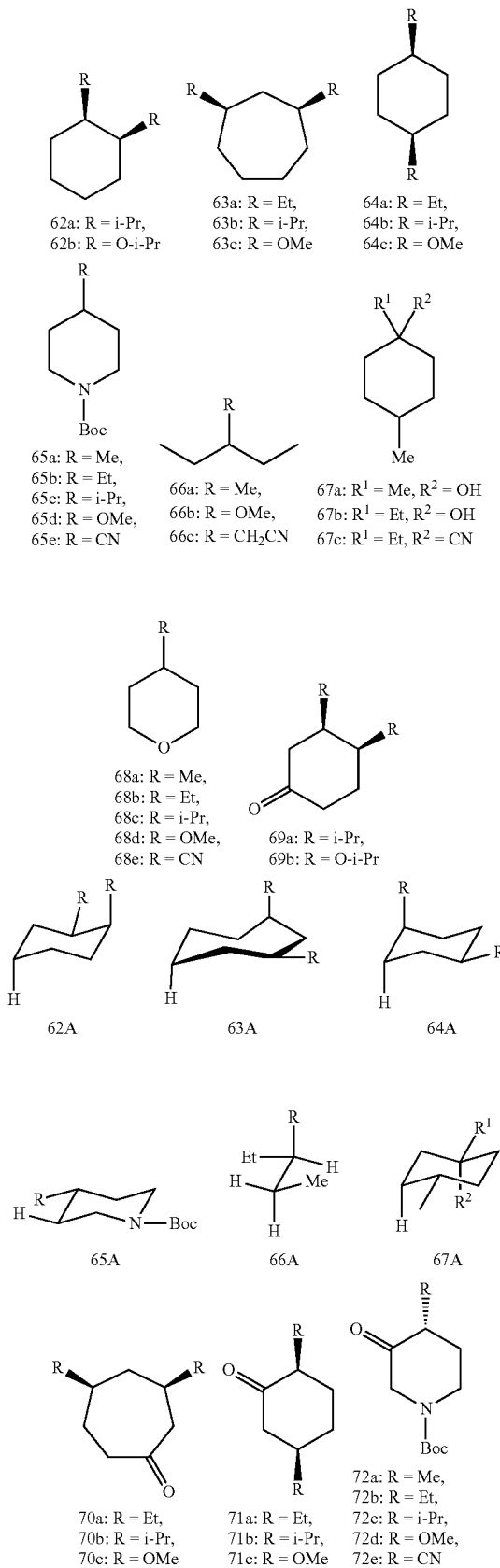

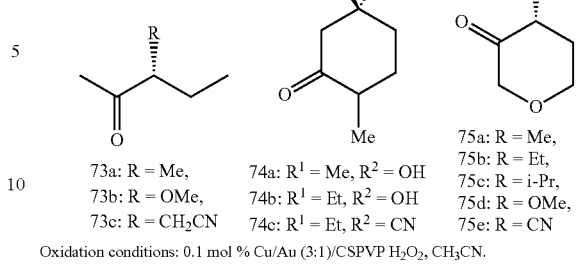

73a: R = Me,
73b: R = OMe,
73c: R = CH$_2$CN

74a: R$^1$ = Me, R$^2$ = OH
74b: R$^1$ = Et, R$^2$ = OH
74c: R$^1$ = Et, R$^2$ = CN

75a: R = Me,
75b: R = Et,
75c: R = i-Pr,
75d: R = OMe,
75e: R = CN

Oxidation conditions: 0.1 mol % Cu/Au (3:1)/CSPVP H$_2$O$_2$, CH$_3$CN.

In another embodiment of the present invention, the catalytic nanoclusters described herein can be used in oxidative C—C forming reactions. In one embodiment, PVP was used in the nanocluster complex, however, other nanocluster/CSPVP complexes can be used. Oxidative cyclization of racemic imine 38 with 0.1 mol % of Pd/Au (3:1)/PVP under O$_2$ (1 atm.) at 30° C. provided 39 and 40 (64% yield) in a ratio of 3:1 (see Scheme 9). Imine 38 was prepared from the coupling of racemic 3-aminocyclohexene and acetophenone. The results suggest that catalytic asymmetric induction can be achieved using symmetrical amines or amines containing no stereogenic center.

Scheme 9.
Results of oxidative C-C bond forming reaction.

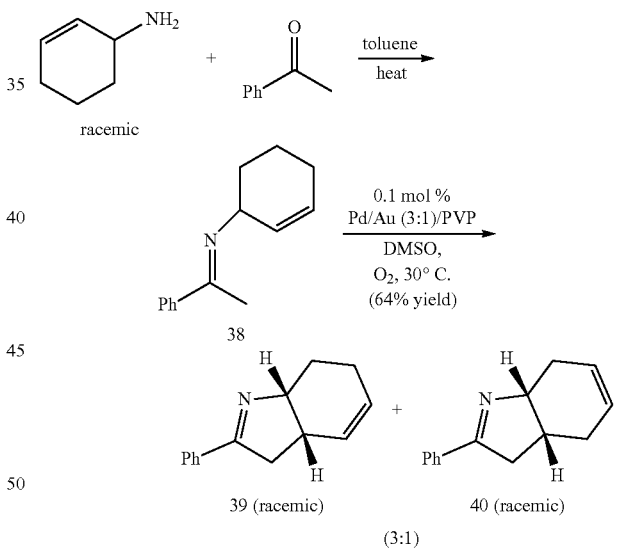

The nanocluster/CSPVP complexes according to certain embodiments of the present invention can be used in other enantioselective C—C bond forming reactions. As shown in Scheme 10, a class of analogous imines, 76a,b, 78a,b, and 80, are subjected to enantioselective ring closing reactions of using 0.1 mol % of Pd/Au (3:1)/CSPVP, and 02 (1 atm) in DMSO separately to give 77a,b, 79a,b, and 81, respectively. Imines 76a and 76b are prepared from amine 76 with Me$_3$Al followed by acetone and ethyl phenyl ketone, respectively, or by heating with a Dean-Stark apparatus (to remove H$_2$O). Amine 76 is made from Birch reduction of benzoic acid accompanied by methylation followed by amide formation via the treatment with carbonyl diimidazole (CDI)

and NH$_4$OH, and Hofmann rearrangement with KOH—Br$_2$ in H$_2$O. The optical purities of the oxidation products are determined via Mosher esters 77c and 77d by reduction of the imino function with NaCNBH$_3$ in MeOH followed by esterification with (R)-Mosher acid chloride and pyridine. The precursor of 80, 3-amino-3-methyl-1,4-pentadiene is made from BocNHCMe(C2Me)$_2$ by the sequence: (i) reduction of the ester functions with NaBH$_4$—CoCl$_2$; (ii) oxidation to the resulting alcohols with IBX-DMSO; (iii) Wittig olefination with Ph$_3$P=CH$_2$; and (iv) TFA (remove Boc group). Optical purity of the products can be assessed through NMR study of the Mosher derivatives by reduction of the imino function of 79 and 81 with NaCNBH$_3$ followed by Mosher acid chloride. Imines 84, derived from amine 82 and ketones 83, can also be subjected to the oxidative C—C bond forming reaction, which leads to spiroimines 85a,b or/and imines 85c,d. The enantioselective C—C bond forming reactions can generate heterocycles having two to three stereogenic centers in one operation.

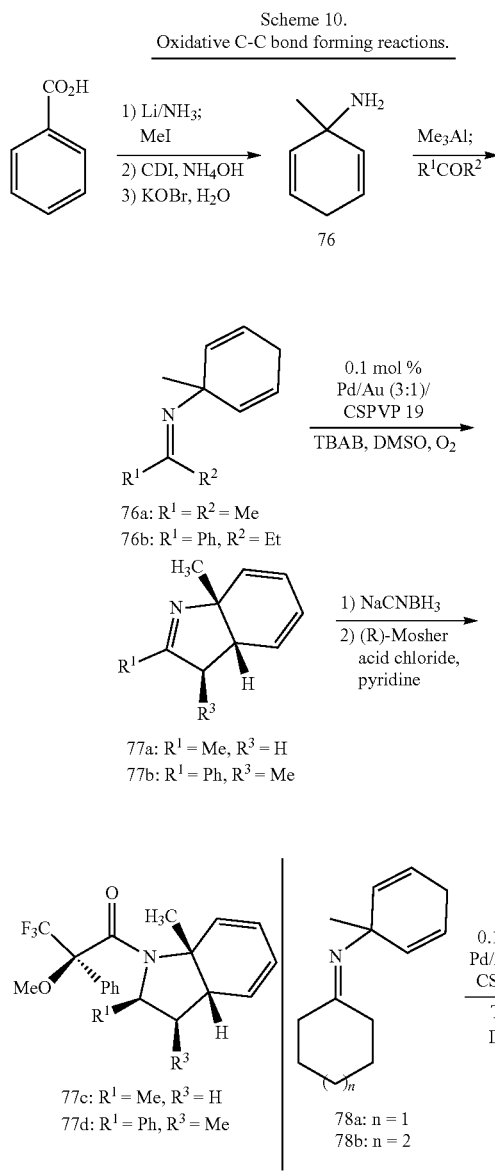

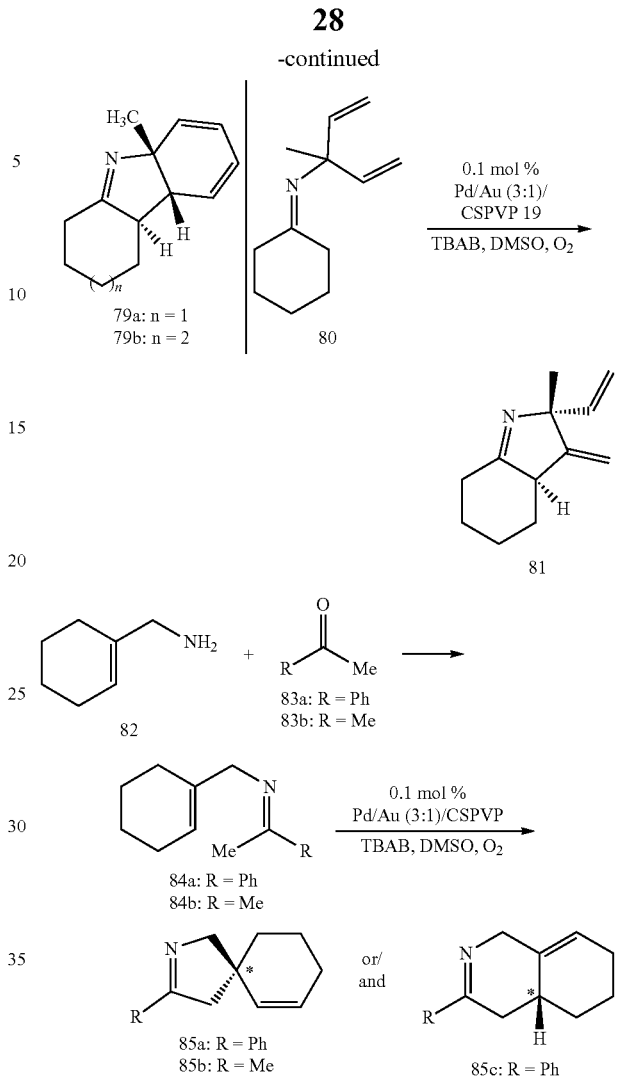

The CSPVP/nanocluster complexes, such as Pd/Au (3:1)-CSPVP, described herein have been discovered to be useful catalysts for the asymmetric dihydroxylation of alkenes, especially cycloalkenes, under aerobic conditions. As shown in Scheme 11, treatment of 1 with 0.1 mol % of Pd/Au (3:1)/CSPVP 18 (0.014 mol %) in water under O2 (2 atm. pressure; to ensure sufficient oxygen is dissolved in the reaction solution) at 55° C. for 12 h gave an 85.2% ee of (1S,2R)-cis-1,2-indandiol [(−)2] (38% yield; based on recovered 1) and an 81% ee of (1R,2R)-trans-1,2-indandiol [(−)-3)] (11% yield; based on recovered 1) along with 23% recovery of 1. The reaction was conducted in a Parr Pressure Reactor, and the products were isolated from silica gel column chromatography. The NMR spectra of (−)-2 and (−)-3 are identical to those reported in the literature and the absolute configurations and optical purities of (−)-2 and (−)-3 were determined based on the reported values of the specific rotations of (−)-2 and (−)-3 and by HPLC using Chiralpak AD(-H) chiral column (FIGS. 1 and 2). Compound (−)-2 has $[\alpha]_D^{22}$=−43.4 (c 0.40, CHCl$_3$) and (−)-3 has $[\alpha]_D^{22}$=−25.0 (0.485, EtOH). Under similar reaction conditions, the use of CSPVP 15 gave an 82.8% ee of (−)-2 and 78% ee of (−)-3. Hence, CSPVP possessing a bulkier C5-R$^1$ substituent, such as 18, provides a greater enantioselectivity.

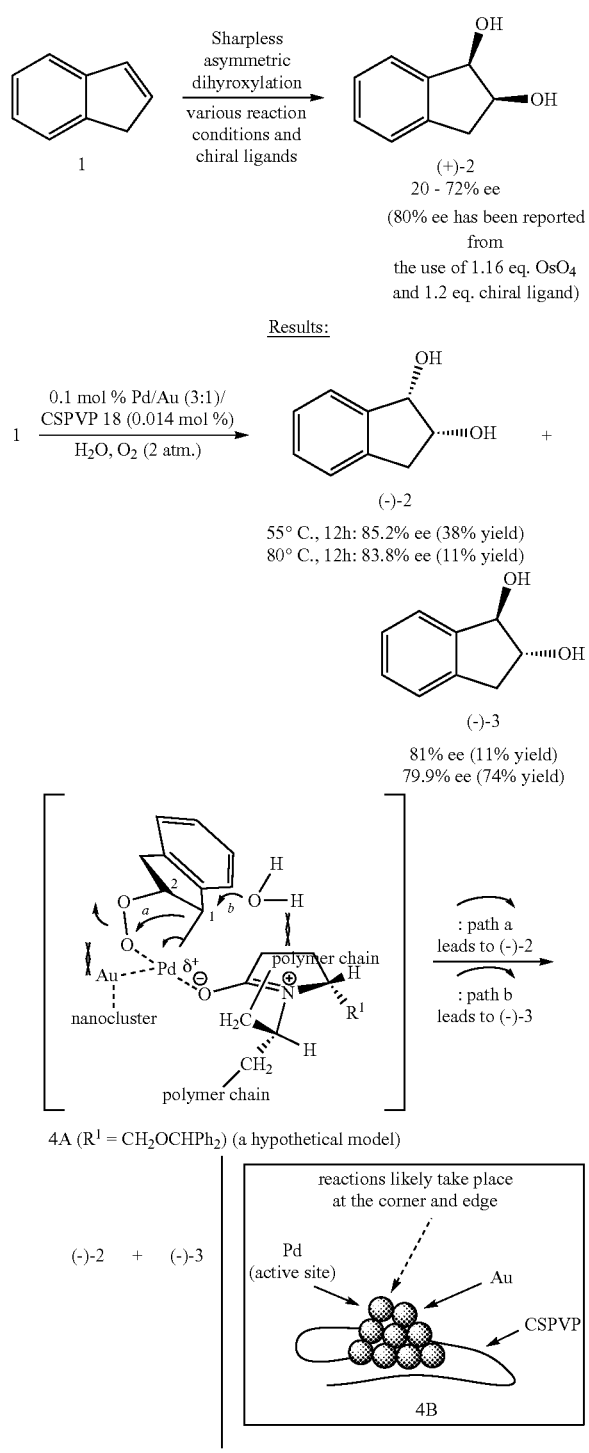

Scheme 11.
Catalytic Asymmetric Oxidation of Indene.

Figure 7:
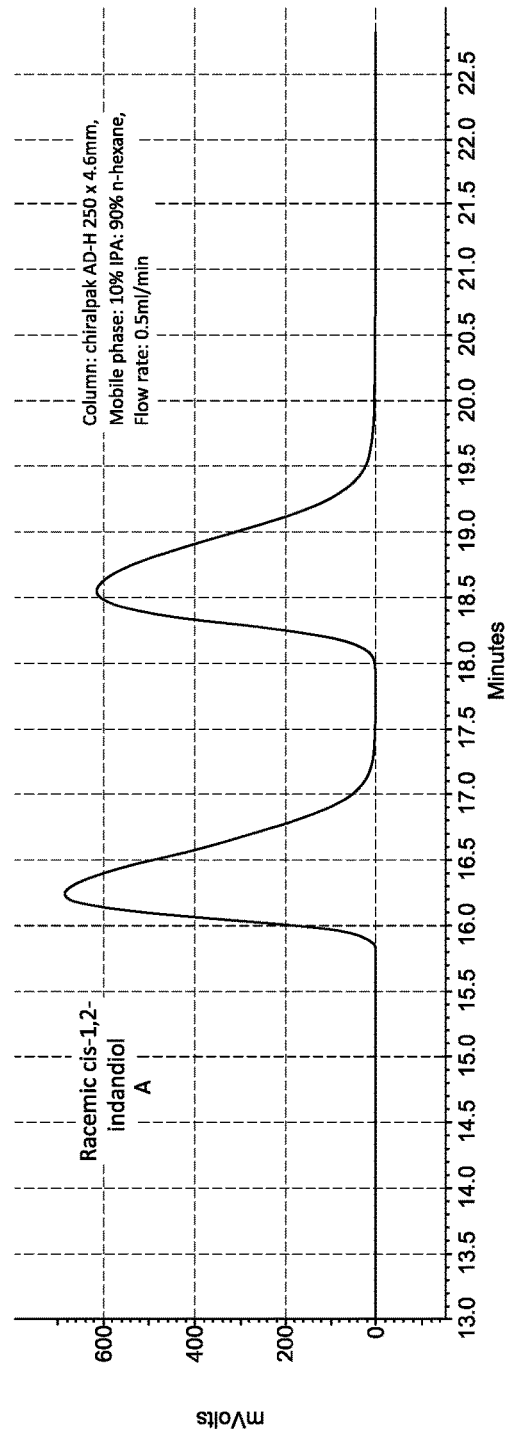
FIG. 7 depicts chiral HPLC chromatograms of racemic cis-1,2-indandiol (A) and optically enriched (−)-(1S,2R)-2 (B) obtained from the catalytic asymmetric oxidation reaction.
Figure 7:
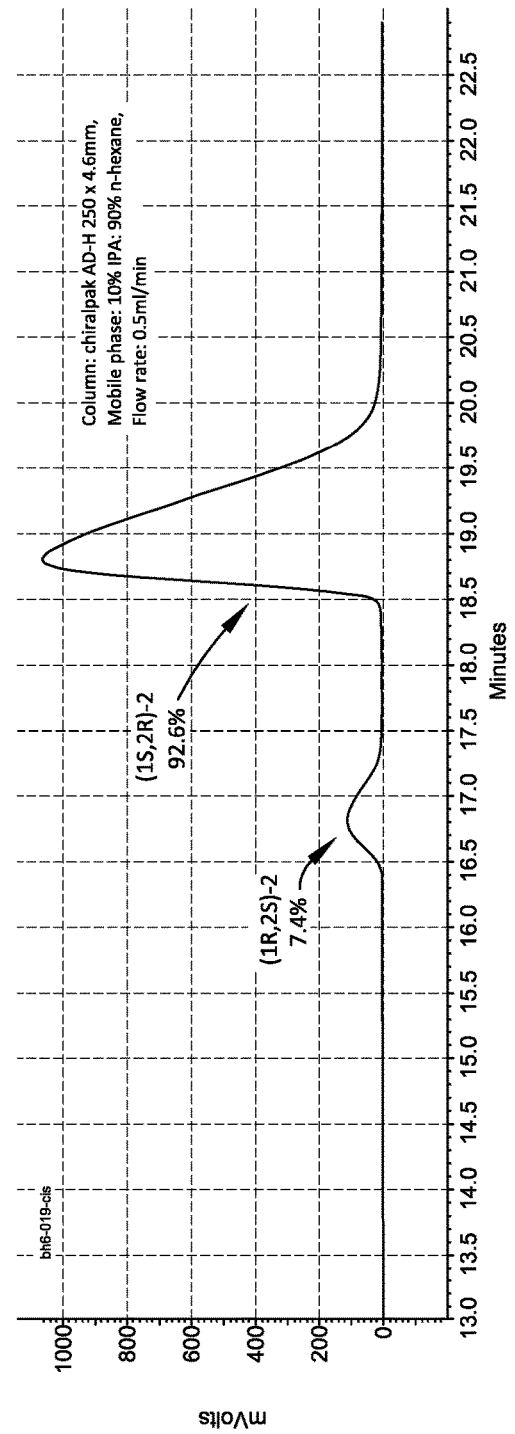
Figure 8:
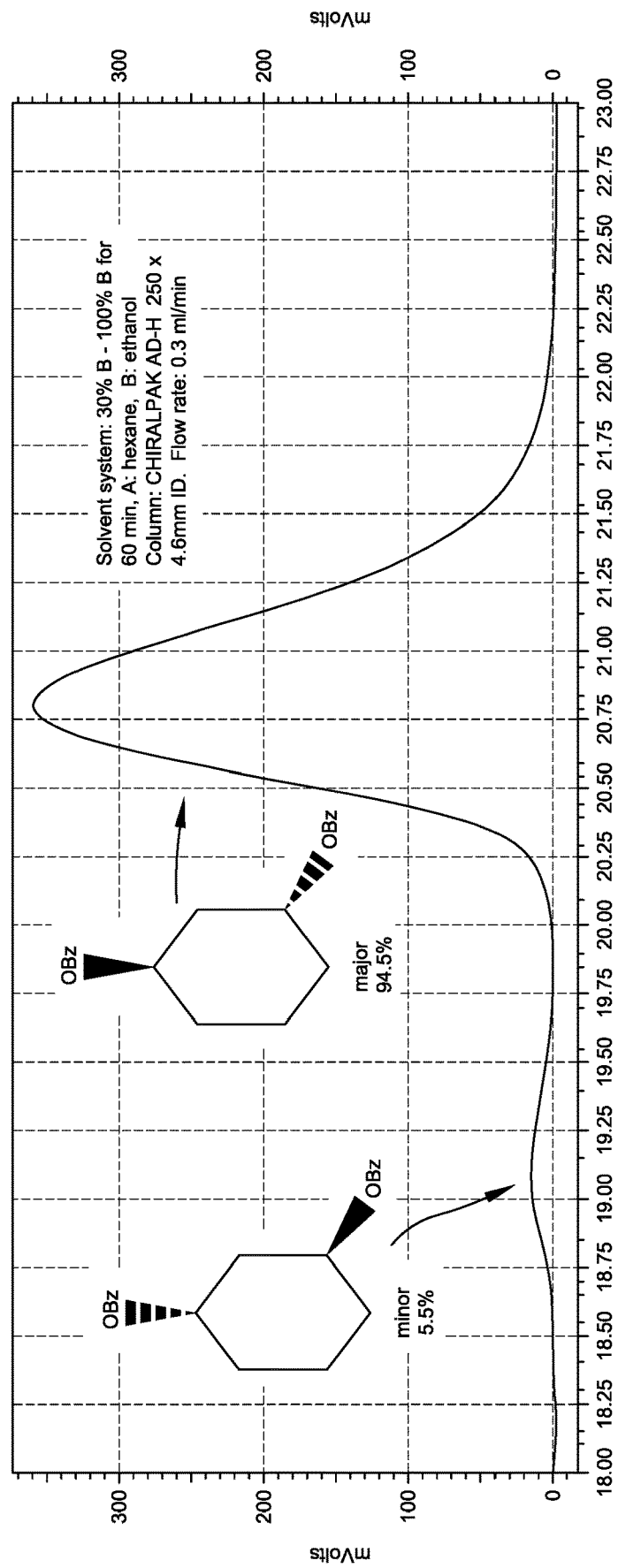
FIG. 8 depicts chiral HPLC chromatograms of racemic trans-1,2-indandiol (A) and optically enriched (−)-(1R,2R)-3 (B) obtained from the catalytic asymmetric oxidation reaction.

The racemic cis- and trans-1,2-indandiols were obtained from Pd/Au (3:1)/PVP—$O_2$ oxidation reaction and subjected to HPLC, see upper panels of FIGS. 7 and 8. No other oxidized products such as ketone byproducts from the oxidation of C1 or C2 hydroxy of 1,2-indandiols or aldehydes or carboxylic acids derived from the cleavage of the C1-C2 bond of 1,2-indandiols were found from the oxidation reactions. When the dihydroxylation reaction was carried out at 80° C. for 5 h, trans-diol (−)-3 was isolated as the major product (74% yield based on recovered indene; 78.9% ee) and cis-diol (−)-2 as the minor product (11% yield based on recovered indene; 83.8% ee) along with 14.5% recovery of indene. The enantiomeric excesses of the two products, determined by HPLC/Chiralpak AD column, are slightly lower than those carried out at 55° C. (HPLC graphs not shown). The product distributions differ as the temperature increases implying two pathways take place.

In general, it is believed that chiral trans-diols are obtained from epoxidation followed by ring opening with hydroxide ion. A hypothetical working model is presented in 4A of Scheme 11 derived from a pseudocyclic peroxypalladation mechanism. A migration of C1 of indene to oxygen (path a; labeled in 4A) leads to (−)-2, and an attack of $H_2O$ at C1 (path b) gives (−)-3.

It is believed that indene approaches the CSPVP-stabilized Pd/Au from the opposite side of the bulky C5-benzhydryloxymethyl group of pyrrolidininone ring, and the aromatic portion of indene orients away from pyrrolidinone to avoid repulsion with the polymer hydrocarbon backbone. The amide function of the polymer and oxygen complex with Pd or Au. The corners and edges of Pd/Au are suggested to be the active sites, and Au pulls electron density from Pd resulting in a greater interaction of Pd with the alkene and oxygen. CSPVP likely wraps around the bimetallic catalysts, and a number of Pd/Au atoms are exposed to the outer face, which undergo oxidation reactions (see, catalyst model 4B in Scheme 11).

In another embodiment, other chiral inducer CSPVPs can be synthesized following the same general sequence of reactions described above for Scheme 1. Particularly, C5-cyclohexyl analog 25 and C5-t-Bu analog 26 can be synthesized (see, Scheme 12). The starting amino acids, N-Boc-L-α-cyclohexylglycine (19) and N-Boc-L-α-t-butylglycine (20) are commercially available (from Matrix Scientific, Columbia, S.C. and Chem-Impex Int., Wood Dale, Ill.). The bulky $R^1$ group would favor the substrates to enter the active site from the opposite side of C5-$R^1$ avoiding steric repulsion (see 4A, Scheme 11).

Two additional CSPVPs 31 and 32 are shown in Scheme 12. A smaller-size C4-$R^2$ substituent oriented in the opposite side of C5-$R^1$ group of the pyrrolidinone ring would hinder incoming substrate from the upper right corner (see hypothetical models 35 and 36) of the lactam ring. A $R^2$=methyl group (smaller group than $R^1$) is used, thereby the larger $R^1$ would maintain a similar reaction active site as that shown in 4A. It is believed that indene likely would enter the active site as shown in structure 35, in which the phenyl ring of indene orients away from C4-$R^2$ of lactam avoiding steric repulsion. The higher energy structure 36 shows a greater repulsion between C4-$R^2$ and the phenyl ring. Treatment of lactams 27 and 28 (intermediates in the syntheses of 21 and 22) separately by a sequence of selenylation, oxidative elimination, and 1,4-addition by lithium dimethylcuprate will provide respective 29 and 30, which can then be converted into CSPVPs 31 and 32 using a similar sequence of reactions as described in Scheme 1.

Scheme 12.
Modifaction of CSPVP.

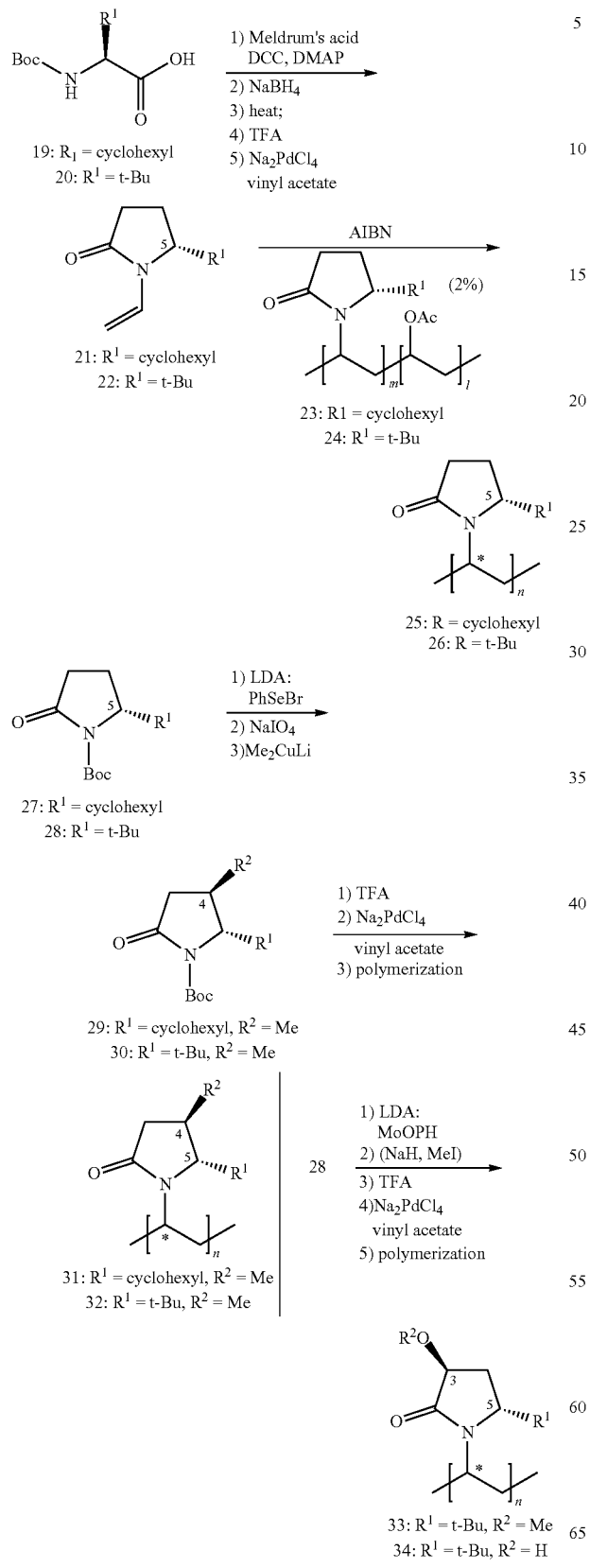

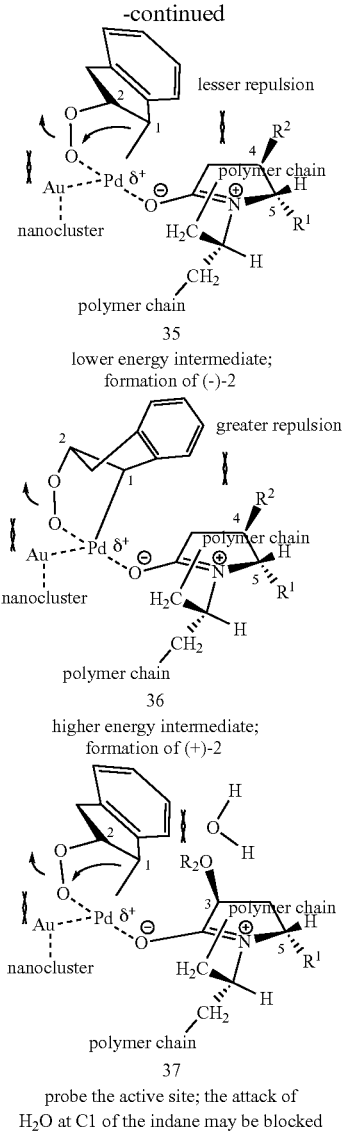

35
lower energy intermediate;
formation of (−)-2

36
higher energy intermediate;
formation of (+)-2

37
probe the active site; the attack of
H₂O at C1 of the indane may be blocked

It is believed that the introduction of a hydroxy or methoxy moiety at C3, such as in CSPVPs 33 and 34, may probe the active site and/or block the attack of $H_2O$ onto C1 of the palladium-peroxide indane intermediate as depicted in 37, which may prevent the formation of (−)-3. Treatment of 28 (a representative example; other pyrrolidinones such as 9 can also be used if needed) with LDA at −78° C. followed by MoO₅·Py·HMPA (MoOPH), removal of the Boc group with TFA, vinylation with $Na_2PdCl_4$-vinyl acetate, and polymerization provides 34. Alternatively, methylation of the C3-hydroxy with NaH-MeI prior to the removal of Boc group gives 33.

The CSPVP catalyst complexes according to the present invention are useful in asymmetric dihydroxylation of other alkenes and cycloalkenes. Scheme 13, below, illustrates further exemplary dihydroxylation reactions with Z-1,2-disubstituted alkenes, E-1,2-disubstituted alkenes, trisubstituted and tetrasubstituted alkenes, labeled compounds 38-48. Olefins 38-47 can be commercially sourced or can be readily prepared in a laboratory. Based on working model 4A (Scheme 11), the corresponding dihydroxylated products are depicted as compounds 49-58.

33

Scheme 13. Alkenes for the Catalytic Asymmetric Dihydroxylation Reactions and Producst.

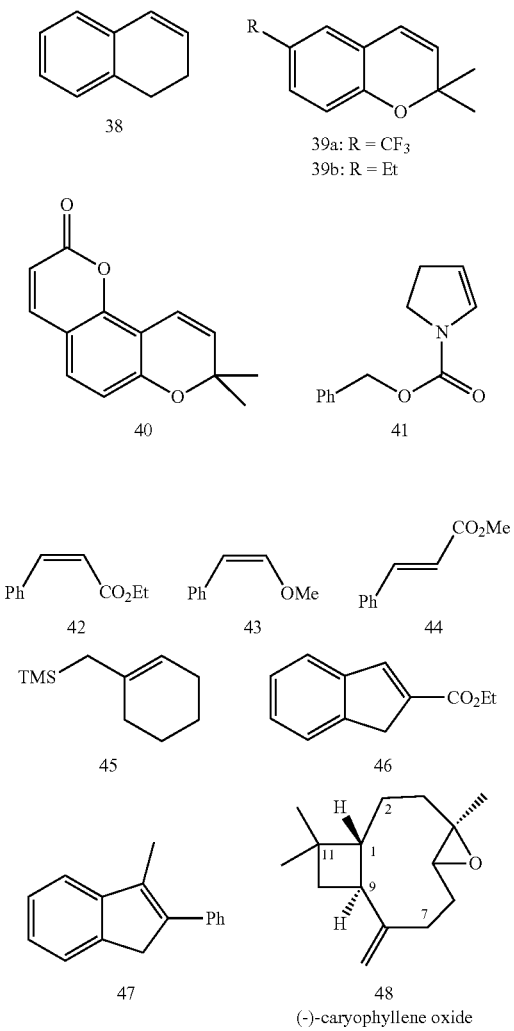

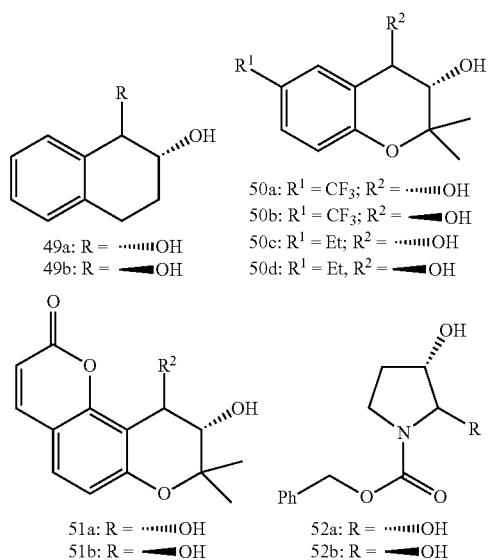

(−)-caryophyllene oxide

Catalytic Asymmetric Dihydroxylation Reaction Reagents and Conditions: 0.1 mol % Pd/Au (3:1)-CSPVP (0.01 mol %), O₂, H₂O, heat

34

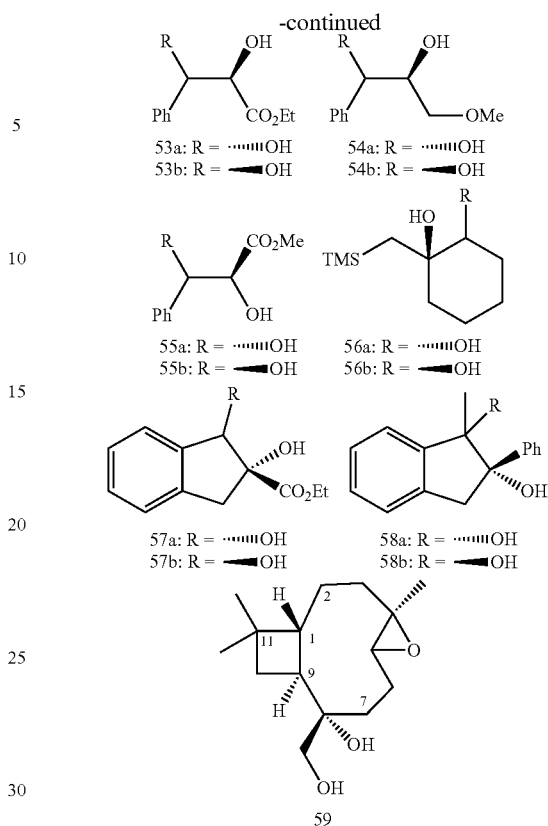

Dihydronaphalene 38 provides a contrast to the asymmetric dihydroxlation of indene discussed above. Sterically hindered alkenes 39a and 39b possess an ether function and electron withdrawing (CF$_3$) or releasing group (Et) in the aromatic ring. Alkene 40 possesses ene ester moiety. Compound 41 comprises an α-N-carbamoyl alkene function. Two acyclic olefins, 42 and 43 possess electron-withdrawing functional groups. E-1,2-Disubstituted alkene 44 comprises a trans-acyclic alkene. Cyclic alkenes 45-47 are trisubstituted or tetrasubstituted. (−)-caryophyllene oxide (48) (from Sigma-Aldrich Inc.) is a complex, medium-size molecule and comprises an epoxide functional ground and a trans-fused four-membered ring.

In certain embodiments, nucleophilic agents such as ammonium acetate or sodium acetate can be used to attack the cyclic peroxypalladium 4A (see Scheme 11) thereby generating chiral trans-1-substituted (amino or acetoxy) 2-indanol.

The foregoing examples are evidence of the broad utility of the CSPVP compounds. The reaction products formed via the asymmetric oxidation reactions disclosed above can be quite useful as reagents in the synthesis of various pharmaceutical compounds wherein various substituents, such as other organic compounds, can be attached at the site of the hydroxyl or ether groups formed in the asymmetric oxidation reaction. In addition the reaction products, which can have a high enantiomeric excess (ee) of one enantiomer, or are substantially enantiopure. These reaction products can also be used in various biosensors as they can be designed to attach to selective biomarkers. The highly pure CSPVP products can be used to bind to various compounds, such as proteins, in order to enable easier separation thereof from a mixture.

Additional embodiments of the present invention, including the synthesis of additional CSPVP compounds and reaction products, are provided in the article entitled, "Chiral-Substituted Poly☐NE☐vinylpyrrolidinones and Bimetallic Nanoclusters in Catalytic Asymmetric Oxidation Reactions" by Hao et al. (*J. Am. Chem. Soc.* 2016, 138, 16839-16848), incorporated by reference herein in its entirety.

In accordance with other embodiments, two additional CSPVPs (69 and 73 in Scheme 14) were prepared and compared to CSPVP 17 (CSPVP 17 is similar to CSPVP 19 from Schemes 1 and 4, described above, and was prepared in accordance with Hao et al., *J. Am. Chem. Soc.* 2016). To study the applicability of syn-dihydroxylation oxidation reactions, ester 62 was treated with 0.5 mol % Pd/Au-17 under 30 psi $O_2$ to give syn-diol 63 in 85% yield and 100% ee (determined by HPLC/chiral column). Neither the anti-diol nor the enantiomer of 63 were detected. The C1-absolute configuration of 63 was determined by conversion into (S)-2-hydroxy-2-methylcycloheptanone (64), a known compound, by the sequence: (i) $LiAlH_4$ reduction; (ii) monomesylation of the 1° alcohol with $MsCl-Et_3N$; (iii) reduction with $LiAlH_4$; and (iv) oxidation with IBX-DMSO. A hydroxyl-directed desymmetrization and oxidative lactonization of 65 to δ-lactone (S)-66 (72% yield; 95% ee) from the oxidation with Cu/Au (3:1)-73 was also discovered. The newly synthesized CSPVP 73 gave the highest ee comparing 17 and 69. Without being bound by any theory, the mechanism may involve the formation of copper ester, followed by addition to the terminal δ-alkene function (providing 65A), fragmentation, and hydrolysis. The absolute configuration S was assumed by comparing the sign of the optical rotation with the literature value of (S)-5-propyl-5-phenyl-dihydrofuran-2-one. The desymmetrization of meso 65 may provide a rapid synthesis of chiral lactones, and the alkene moiety can be further functionalized. Alcohol 65 was readily prepared from the addition reaction of 2 eq of 3-butenylmagnesium bromide and isopropyl benzoate.

Scheme 14
Catalytic asymmetric oxidations and syntheses of CSPVPs possessing a greater steric hindrance than 17.

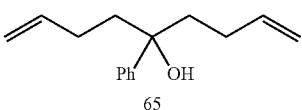

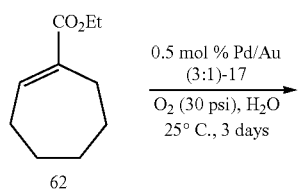

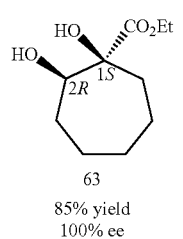

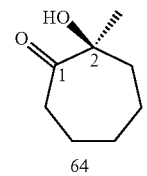

64
$[α]_D^{23} = -71°$ (c 0.24, $CHCl_3$)
(S-configuration)

4 mol % Cu/Au (3:1)-CSPVP
────────────→
30% $H_2O_2$, $CH_3CN$,
50° C., 7 days

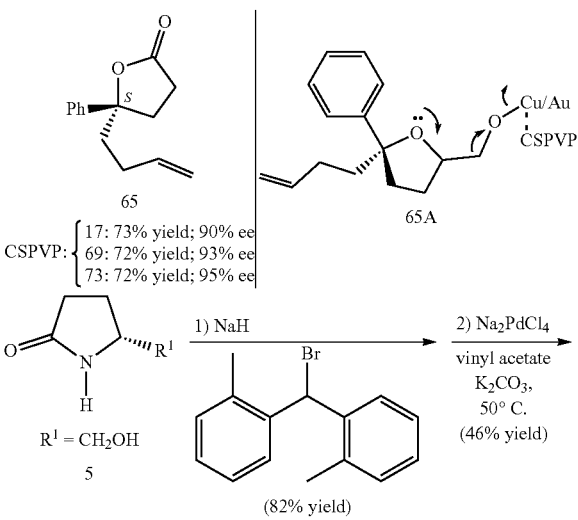

CSPVP: { 17: 73% yield; 90% ee
69: 72% yield; 93% ee
73: 72% yield; 95% ee }

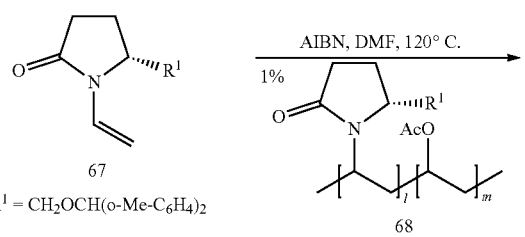

$R^1 = CH_2OH$
5

(82% yield)

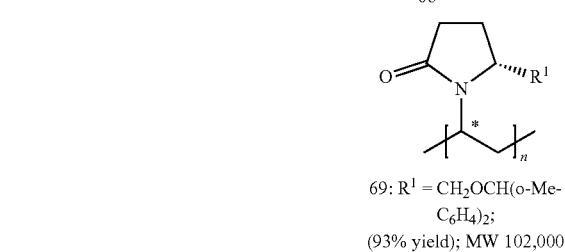

67
$R^1 = CH_2OCH(o-Me-C_6H_4)_2$

AIBN, DMF, 120° C.
────────────→
1%

68

69: $R^1 = CH_2OCH(o-Me-C_6H_4)_2$;
(93% yield); MW 102,000

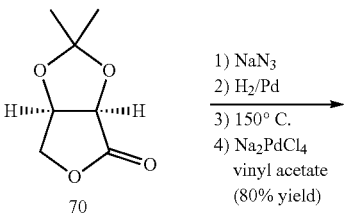

70

1) $NaN_3$
2) $H_2/Pd$
3) 150° C.
4) $Na_2PdCl_4$
   vinyl acetate
(80% yield)

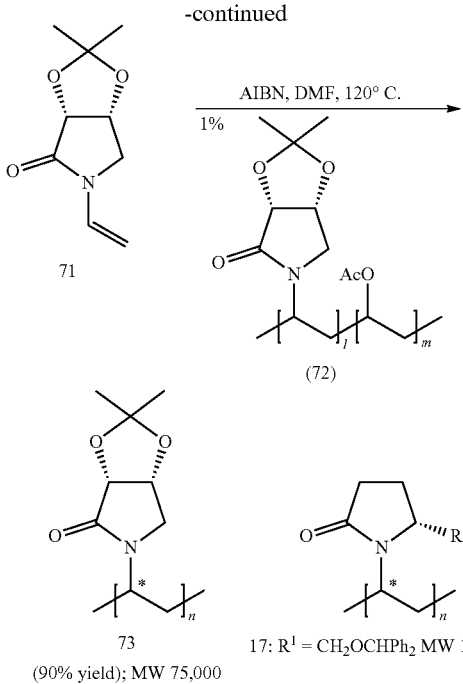

Scheme 14 is described in more detail below. To improve the enantioselectivity in C—H oxidation of CSPVPs, polymers 69 and 73 were synthesized through a similar protocol as described in Scheme 1. Without being bound by any theory, it is believed that the C=O of amide function of the pyrrolidinone ring complexes with Pd/Au and the C5 substituent would block one side of the pyrrolidinone plane opening up the opposite side for the substrate to enter for oxidation. Hence, polymer 69 containing a di-(o-tolyl) methoxymethyl group at C5, a bulkier group than that in 17, and polymer 73 possessing C3,4-acetonide in the pyrrolidinone ring were designed and synthesized. Alkylation of 5 with NaH and di-(o-tolyl)methyl bromide followed by vinylation and polymerization to give polymer 69 (Scheme 3). Polymer 73 was similarly synthesized from vinyl lactam 71, which was obtained from lactone 70 via the sequence: (1) ring opening with NaN$_3$-DMF; (2) reduction with H$_2$/Pd—C; (3) lactonization at 150° C.; and (4) vinylation with Na$_2$PdCl$_4$, vinyl acetate and K$_2$CO$_3$. 65 was used to examine the enantioselectivities, and 73 provided the highest ee in the oxidative ring closing reaction among the three CSPVP 17, 69, and 73. The preparation of 2,3-O-isopropylidene-D-erythronolactone 70 from erythorbic acid has been reported previously. [Organic Syntheses, Coll. Vol. 7, p. 297 (1990)].

In certain embodiments, optical yields may be improved by using polymers 69 or 73 over polymer 17. As shown in the conversion of 65 to 66, CSPVP 17, 69, and 73 achieved 90, 93, and 95% ee, respectively. In certain embodiments, the size of geminal dimethyls (in the acetonide) of 73 are changed to diethyls, which is believed to provide a greater steric hindrance and further enhance enantioselectivity.

In certain embodiments, the nanoparticle clusters comprising the CSPVP can be used in asymmetric oxidations of acyclic diols and cyclic polyols. Acyclic chiral β-hydroxyketones and α-hydroxyketones are useful synthetic intermediates in organic synthesis. They are often parts of the bioactive natural products including amphidinolide B and tasiamides. Thus, the asymmetric oxidation of representative acyclic diols, meso-74 and meso-76, using Pd/Au-73 and O2 (Scheme 15) may be used to examine whether the oxidative sites for syn-diols may hold in acyclic molecules, forming respective (3R,4S)-75 (R$^1$=Me) and (S)-77. Meso-74 is prepared by following a reported procedure, and meso-76 is prepared from cis-3-hexene and OsO$_4$-NMO. Other meso-diols (R$^1$=R$^2$=alkyl or aryl) can also be used. Cyclic triols, such as meso syn-triol 78 and anti-triol 80 (derived from mono-acetylation of methyl β-D-glucopyranoside) can also be used, which is believed to result in (2S,3S)-79 and keto-sugar 81. Preparation of meso-78 has been reported and the conversion of (2S,3S)-79 to ester derivatives of 2-arachidonoylglycerol (2-AG) has appeared. Endogenous 2-AG binds to CB1 and CB2 cannabinoid receptors. The derivatives may lead to the design of selective CB1 antagonists for the treatment of obesity and nicotine and alcohol dependence. Selective oxidation of unprotected or partially protected carbohydrates is a challenging process and the resulting keto function of 81 can be converted to C—C, C—N, or C—S group, achieving various bioactive amino- and thiosaccharides. The asymmetric oxidation of acyclic diols and cyclic polyols described herein will broaden the application.

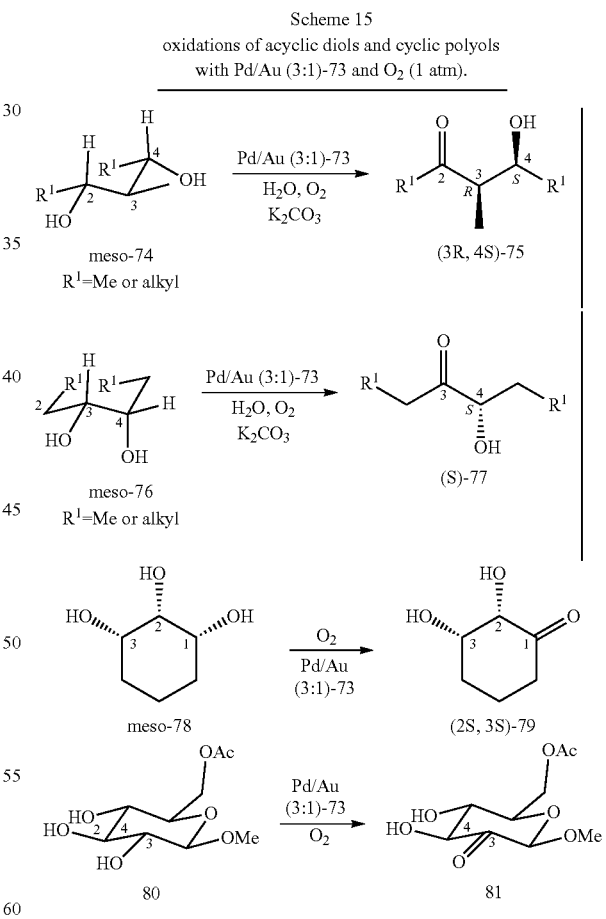

Scheme 15
oxidations of acyclic diols and cyclic polyols
with Pd/Au (3:1)-73 and O$_2$ (1 atm).

In certain embodiments, the nanoparticle clusters comprising the CSPVP can be used in asymmetric oxidation of alkenes. A number of representative alkenes can be used in the oxidation with 0.5 mol % Pd/Au (3:1)-73 and O2 (Scheme 16). For example, alkenes such as 82-86, which do not provide high ee's in the Sharpless reactions, can be used.

Scheme 16 lists the highest reported % ee's obtained from 82, 83, 84, 85, and 86 from the Sharpless oxidation. In certain embodiments, the present invention can achieve greater % ee in the oxidation of these alkenes. It is believed that $\eta^2$-peroxido $Pd^{II}$ intermediate approaches terminal alkenes, 82 and 83, from the Si-face (of C2), resulting in (S)-90 and (S-91, respectively. It is also believed that the hydroxyl group of trans-alkenes 84 complexes with Pd/Au, forming (2S,3S)-92. Similarly, oxidation of 85 should give (S)-93 (Re-face selective). The hemiacetal generated from the dihydroxylation reaction undergoes α-elimination to form aldehyde followed by cyclization with the γ-hydroxyl group and oxidation to give lactone 93. It is further believed dihydropyran 86 attacks from the Re-face of 86 to give (R)-94. Low to good ee's in the Sharpless dihydroxylation of cyclic enamides, ene sulfonamides, and dihydropyridine have been reported. However, asymmetric oxidations of 87, cyclic enone 88, and cyclic enamide 89 have not appeared. The preparations of 87, 88, and 89 have been reported. It is believed that the oxidations of 87-89, in which the $R^L$ group possesses bulky Boc group, lead to (3S,4R)-95, (4S,5S)-96, and (3S,4S)-97, respectively. As understood by those in the art, these chiral heterocycles are difficult to obtain by other methods. The resulting hydroxylated piperidines and pyrrolidinone can be converted into bioactive I-deoxyazasugars for the inhibition study of diabetes, cancer, and viral infections.

Scheme 16 catalytic asymmetric oxidation of alkenes with 0.5 mol % Pd/Au (3:1)-73 (or 17) and $O_2$ (2 atm).

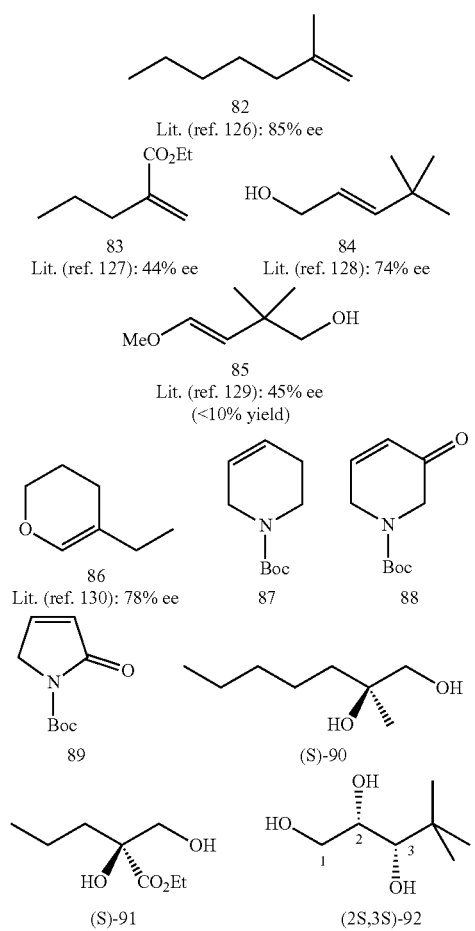

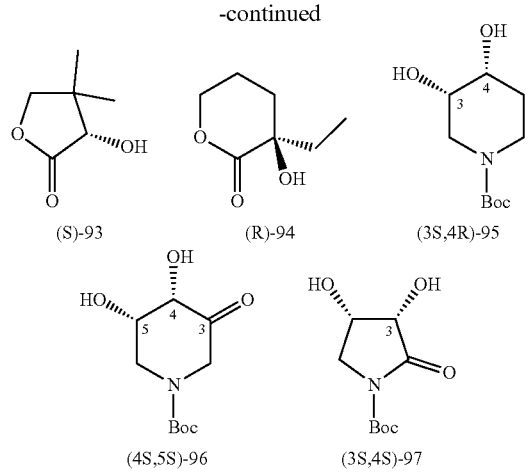

In certain embodiments, the nanoparticle clusters comprising the CSPVP can be used in catalytic asymmetric C—H oxidation of alkanes and cycloalkanes. 98-104 (Scheme 17) were selected using Cu/Au (3:1)-73 (or 69)-$H_2O_2$. It is believed that in the oxidation of 98, the hydroxyl group directs the oxidation, resulting in formation of 105 ($R^1$=aryl, $R^2$=Me). Other analogs of 98 containing different $R^1$ and $R^2$ may also be used. The facile oxidative lactonization of 65 to 66 provided a convenient method to various 5,5-disubstituted lactones (Scheme 14). Various tertiary alcohols 99 (n=0-3) can be used for the formation of 106. Functional group interconversion of analogs of 106 may lead to various bioactive spirolactones, such as yaoshanenolides A and B. The reaction of 99, n=0, may lead to β-lactone 106, but the γ-lactone may also form). It is believed that the oxidations of 100 and 101 separately will give 107 and 108, respectively. It is believed that greater ee's result, since the smaller $R^S$=Me group in 100 and 101 would lower the TS activation energy. It is believed that oxidation of 102 using Cu/Au-69S (stereoisomer of 69 containing C5-S configuration in the pyrrolidinone ring, derived from N-Boc D-(R)-amino acid 1R) will give (R)-109. It is believed that Cu/Au oxidation of nitrogen containing heterocycles produces different regiochemistry from reported Fe(PDP) complexes (which oxidized the α-carbon of the nitrogen), and thus the oxidation of 103 and 104 can be used. Like the hydroxyl function in 98, it is believed that the carbonyl of ester group directs the C—H oxidation, since amides (such as PVP) do not undergo oxidation a to the nitrogen. Hence, the bulky $R^L$, N-Boc group, orients at C1, providing 110. Oxidation of N-Boc L-proline ester 104 may reveal the directing effect of the ester group in C—H oxidation. Chelation controlled reduction of 111 using ($CeCl_3.7H_2O$—$NaBH_4$) (chelate with the ester group) followed by removal of the Boc group with TFA gives 4R-hydroxyproline methyl ester, a methyl protected natural amino acid and a key fragment of the antifungal natural products, pneumocandin B0, and caspofungin. Hydroxyl derivative of 107 has been used in the total synthesis of anticancer natural product prevesol B. Compounds 98 and 99 can be prepared by the addition reactions of 2 eq. of alkylmagnesium bromides or alkenylmagnesium bromides (or the corresponding lithium reagents) respectively with ethyl alkanoates (or substituted benzoates). Molecules 100 and 101 can be prepared by following the reported procedures. Compound 103 and methyl N-Boc-proline 104 are commercially available (Chem Impex International, Wood Dale, Ill.). Alcohol 102 can be made from the mono-silylation of 1-(2-hydroxyethyl)pentanol with 1 eq TBSCl-Et₃N. Compounds 107-109 can be used in bioactive natural products synthesis. The CSPVPs described herein advantageously provide highly functionalized chiral molecules, which can be transformed into bioactive molecules.

Scheme 17 C-H oxidation of alkenes and cycloalkanes using Cu/Au (3:1)-CSPVPs (69 or 73) and H₂O₂.

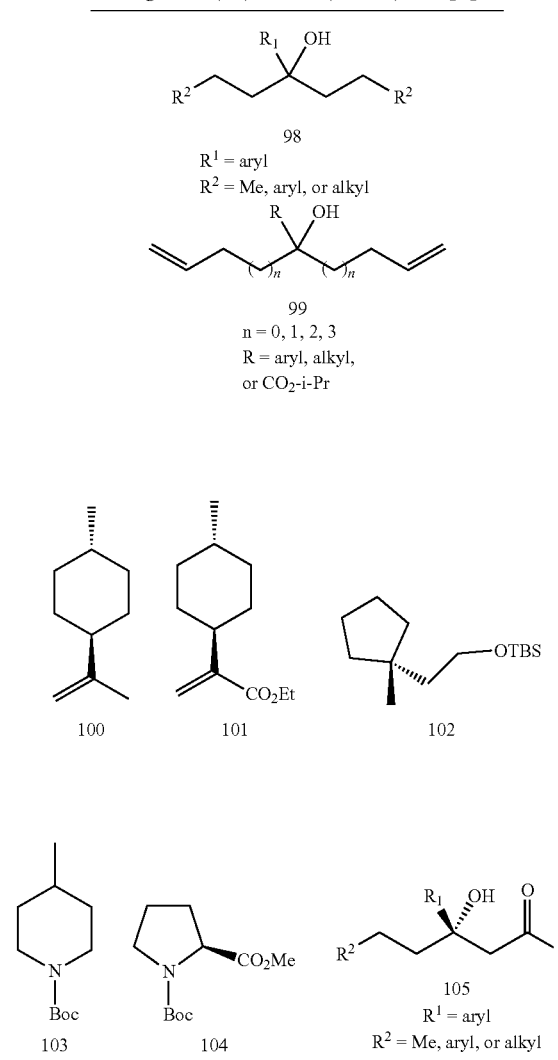

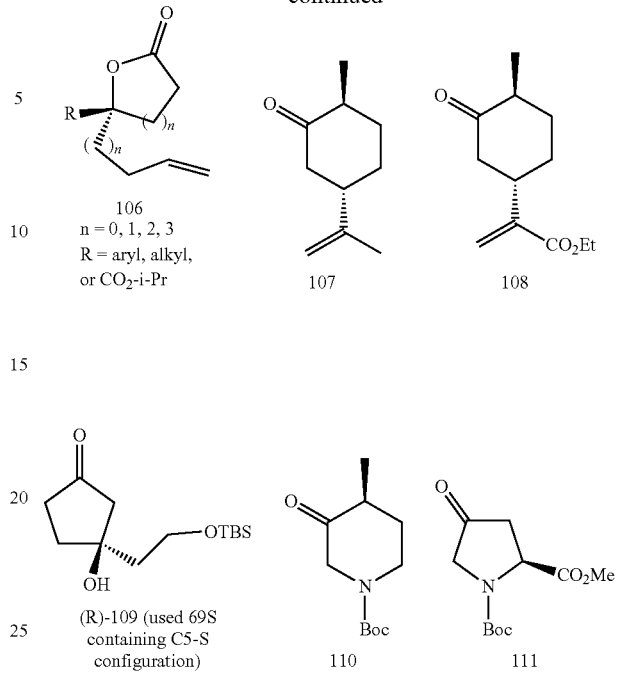

Embodiments of the present invention may be used in synthetic applications of catalytic asymmetric oxidation reactions in the total syntheses of bioactive natural products. Scheme 18 illustrates four applications of the C—H oxidation products, 107-109 and 63 in the total syntheses of bioactive natural products. Fabianine (114), an inhibitor of β-glucuronidase, was isolated from *Fabiana imbricata* shrub in central Chile and has been used to treat kidney and bladder infection. α-Hydroxylation of 107 with LDA in THF and MoOPH gives 112. Conversion of 112 to fabianine precursor 113 can be carried out by the sequence: (i) Wittig olefination with 2 eq. of Ph₃PCHCH₂CH(OTBS)Me; (ii) removal of the TBS groups with n-Bu₄NF; (iii) bromination of the resulting diol with Ph₃P and CBr₄; and (iv) ring closing and oxidative dehydrogenation with NH₄OAc in ethanol under heat. In the olefination reaction, C4,5-cis-alkene is believed to form as the predominant product, since the trans-isomer will have a greater repulsion with the C10 methyl group. The Wittig reagent will be generated from 1-bromo-3-(t-butyldimethylsilyloxy)butane and Ph₃P followed by phosphor ylide formation with n-BuLi.

Scheme 18
Application in the total synthesis of biozctive natural products.

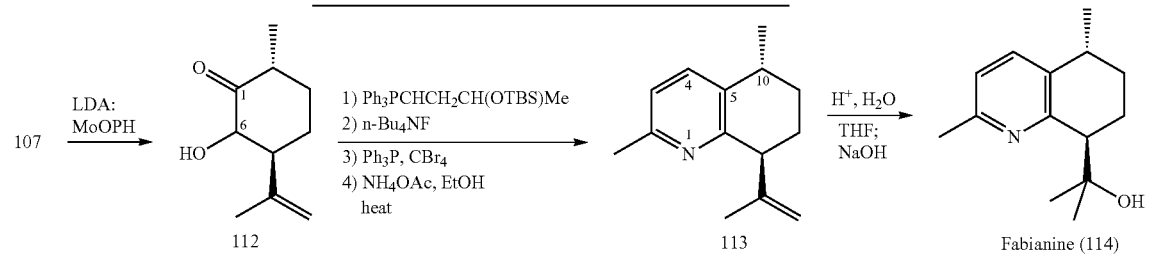

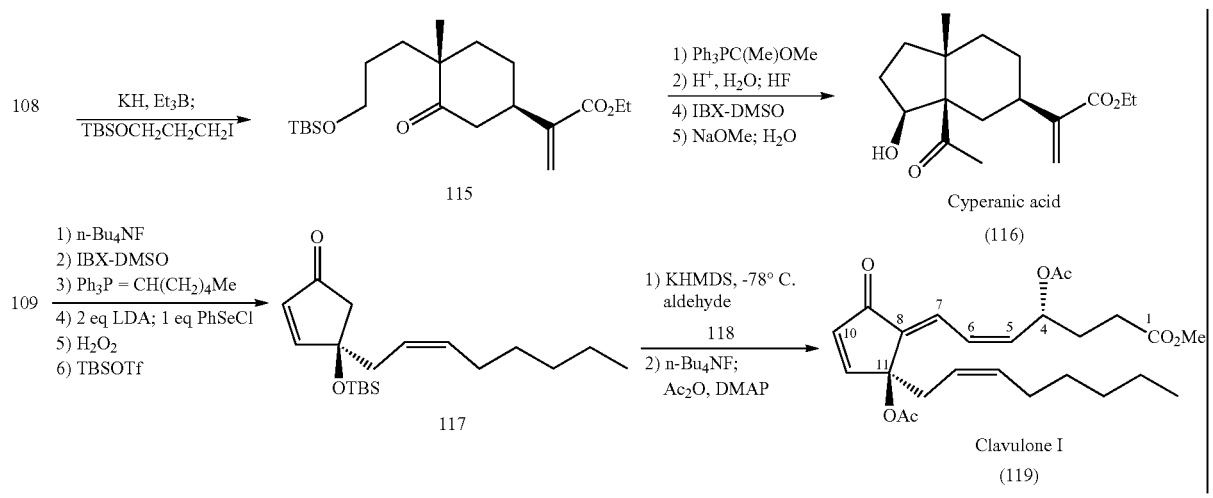
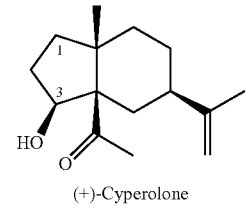
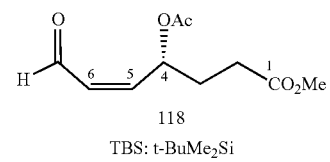
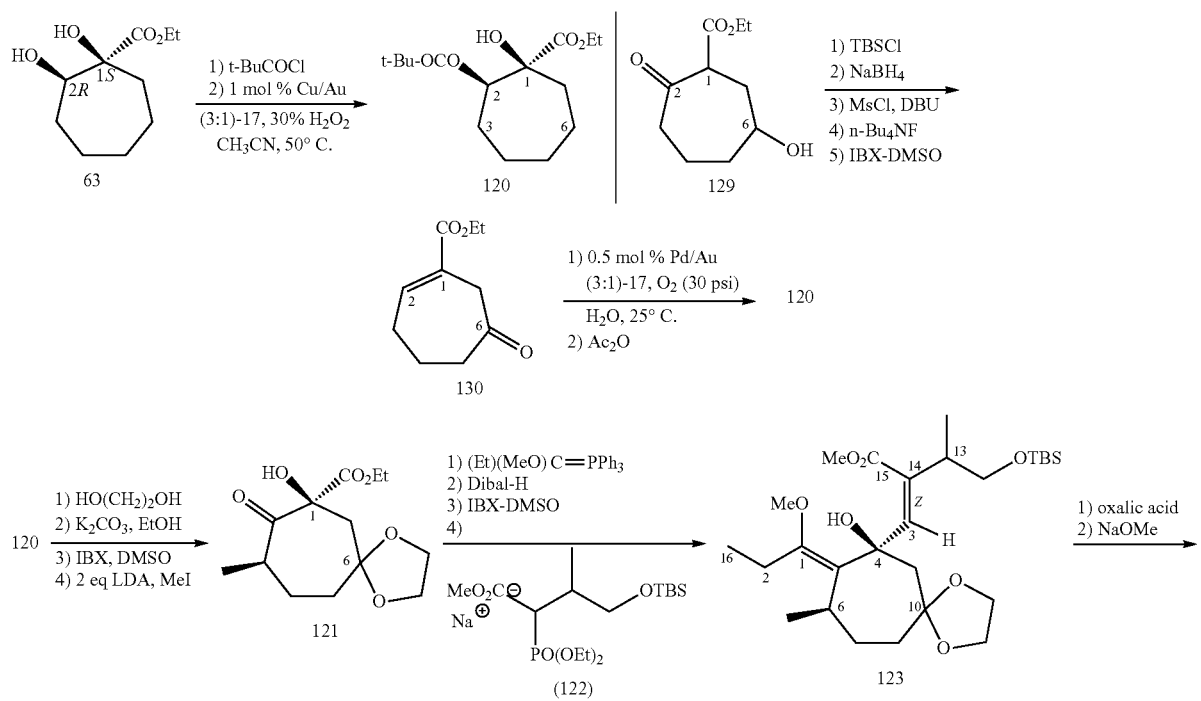

-continued

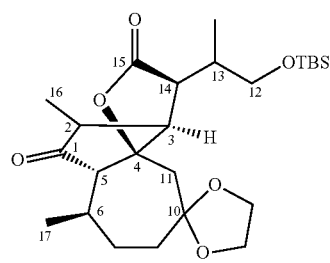

1) NaBH₄
2) Ac₂O
3) TsOH, Me₂CO
4) n-Bu₄NF
5) IBX-DMSO
6) NaOMe

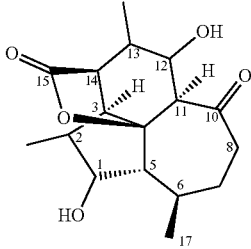

124

1) 2 eq TBSCl
2) 1 eq Dibal-H
3) MsCl, Et₃N
4) DBU

125

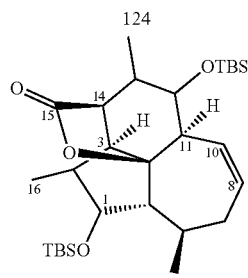

126

1) CHBr₃, NaOH
2) CuCN, MeLi; MeI
3) n-Bu₄NF

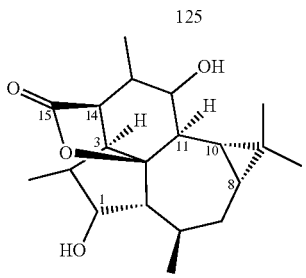

127

1) MsCl; DBU
2) LDA MoOPH

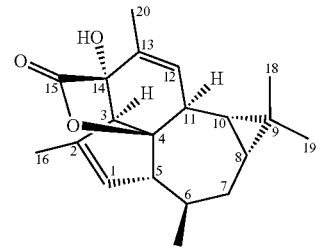

Euphorikanin A
(128)

Cyperanic acid (116), a sesquiterpene from Mediterranean plant Dittrichia viscosa, belongs to the eudesmane natural products including cyperolone (116A). The total synthesis and bioactivity of cyperanic acid have not been reported, and eudesmane sesquiterpenes have been used for the treatment of gynecological diseases. Enolate formation of 108 under thermodynamic conditions with KH and triethylborane at −78° C., followed by 1-(t-butyldimethylsilyloxy)-3-iodopropane provides 115. The enolate ion should react with the alkyl halide from the equatorial face, opposite to the bulky C5-alkenyl group producing thermodynamically stable product. Wittig olefination of 115 with Ph₃PC(Me)OMe, followed by hydrolysis of the enol methyl ether with aqueous acid and in situ removal of t-butyldimethylsilyl (TBS) group with HF, oxidation of the resulting primary alcohol with IBX-DMSO, and ring closing and hydrolysis of the ester group with NaOMe will afford (+)-cyperanic acid (116). The keto function of 115 is more reactive than the ene ester moiety with the Wittig reagent. Formation of five-membered rings via an (enolexo)-exo-trig is a favorable process according to the Baldwin's rule, and the resulting OH and ketone would be cis. (+)-Cyperolone (116A) can similarly be synthesized from 107 by following a similar sequence of reactions as that described for 116.

Marine prostanoids such as clavulones were isolated from soft coral Clavularia viridis and have attracted a number of syntheses because of their bioactivities, including inhibitions of phytohemagglutinine-induced peripheral blood mononuclear cells and human gastric cancer cells. Ketone (R)-109 is converted to 117 by the sequence: (1) removal of the TBS group by n-Bu₄NF; (2) oxidation with IBX-DMSO to aldehyde; (3) cis-olefination with Ph₃P═CH(CH₂)₄CH₃; (4) selenylation with 2 eq of LDA (one equiv is used to remove the proton of OH) in THF at −78° C. followed by PhSeCl; (5) oxidation with 1 eq of H₂O₂ (β-elimination); and (6) silylation of the hydroxyl group with t-butyldimethylsilyl triflate-2,6-lutidine. The aldehyde function should react selectively in the presence of ketone. Compound 117 is a key intermediate in various reported total synthesis of clavulones. In the deprotonation reaction with LDA, the hindered base should mainly remove the more accessible proton from C-5. Following the reported synthesis, treatment of 117 with potassium hexamethyldisilazide (KHMDS) at −78° C. followed by aldehyde 118, removal of the silyl protecting groups with n-Bu₄NF, and acetylation of the two hydroxyl groups with acetic anhydride and DMAP will furnish clavulone I (119). The preparation of aldehyde 118 has been reported.

Euphorikanin A (128), a diterpene, is isolated from the roots of perennial herb Euphorbia kansui. The roots are used for the treatment of ascites, asthma, edema, epilepsy, and soreness. It contains a unique 5/6/7/3 fused ring system and has not been synthesized previously. A total synthesis of 128 from 63, containing the needed stereochemistry and functional groups, is outlined in Scheme 18. Compound 63 has been prepared in optically pure form (Scheme 14), and can be acylated with t-BuCOCl-pyridine followed by catalytic oxidation with Cu/Au (3:1)-17 and 30% H₂O₂ to give 120.

The t-Bu group should block oxidation at C3, and 17 will direct the oxidation at C6. Ketallization of 120 with ethylene glycol and pyridinium tosylate (catalytic amount) followed by removal of the ester group, oxidation with IBX-DMSO, and α-methylation with 2 eq. LDA-MeI will lead to 121. Methyl iodide should react with the enolate ion from the opposite face of the C1 bulky ester group, and the C3-α-isomer can be isomerized with a weak base. Wittig olefination of 121 with ylide (Et)(MeO)C═PPh₃ followed by reduction and oxidation to the corresponding carboxaldehyde (C1), and Horner-Wadsworth-Emmons reaction with sodium salt 122 will give 123. α-Substituted phosphonate anion with sterically encumbered aldehydes provided the Z-unsaturated esters. Phosphonate 122 is derived from the bromination of methyl 4-(t-butyldimethylsilyloxy)-3-methylbutanoate followed by triethylphosphite and NaH. The stereochemistry at C3 likely dictates the stereochemistry in the subsequent intramolecular 1,4-addition reaction. Hydrolysis of the C1-vinyl ether function of 123 with 0.1 M aqueous oxalic acid, and ring closing with NaOMe gives 124. The 1,4-addition of enolate (C2) to alkene C3 should take place from the Re-face (C14) of the ene ester, since both ester C═O and the enolate oxygen chelate with the Na, which in turn directs the (S)-stereochemistry at C3. The ketal is stable under oxalic acid condition. Compound 124 can be converted to diol 125 by the sequence: (1) reduction of C-keto with NaBH₄; (2) acetylation with Ac₂O-pyridine; (3) removal of the ketal with TsOH-acetone at r.t.; (4) desilylation with n-Bu₄NF; (5) oxidation with IBX-DMSO; and (6) intramolecular aldol reaction with NaOMe-MeOH. C-11 H is epimerizable and C11-α-H isomer 125 will be used. Protection of the two hydroxyl functions of 125 with 2 eq. TBSCl-Et₃N followed by reduction of C10-keto with Dibal-H, mesylation with MsCl-Et₃N, and β-elimination with DBU will give 126. Cyclopropanation of C8 alkene of 126 with CHBr₃—NaOH followed by Me₂CuLi then Me, and removal of TBS groups will afford 127. The dibromocarbene should add to the alkene from the less hindered α-face. Mesylation of diol 127 with 2 eq. of MsCl-Et₃N followed by β-elimination with DBU, and α-hydroxylation (α-face is more accessible than β-face) of the lactone with LDA-MoOPH or lithium HMDS-t-BuOOH-pyridine-CuI will furnish euphorikanin A (128). If the stereochemistry at C3 of 124 is R-configuration, the E-alkene (C3═C14) of 123, which can be prepared from the phosphorane Ph₃P═C (CHMeCH₂OTBS) with the aldehyde (derived from 121), can be cyclized. If 120 cannot be obtained from 63, it can be made from 129 by protection with TBSCl followed by reduction of the keto with NaBH₄, β-elimination with MsCl and DBU, removal of TBS group and oxidation with IBX to give 130. Oxidation of 130 with 0.5 mol % Pd/Au (3:1)-17-O₂ followed by 1 eq t-BuCOCl-pyridine will give 120. Alcohol 129 can be made from the treatment of ethyl 2-oxo-5-hepten-1-carboxylate with Chx₂BH•THF or Sia₂BH followed by H₂O₂—NaOH. Keto function is stable under dicyclohexylborane reaction conditions.

Embodiments of the present invention may also be used in "late-stage" aliphatic C—H oxidation, C—H azidation, and C—H chlorination of complex molecules, which can modify the pharmacological property and improve bioactivity of the molecules. The newly installed ketone group can be converted into various functionalities, leading to a library of compounds for the screening of bioactivity. Most of the reported oxidation, azidation, and chlorination often take place at the tertiary C—H, allylic C—H, or benzylic C—H bond due to a lower bond energy comparing with that in CH₂ and CH₃ bonds. (+)-sclareolide (60) was oxidized regioselectively at the rigid and less hindered C2-CH₂ to give 2S-hydroxy 61. Embodiments described herein may be used to study the generality, regioselectivity, and predictability of the oxidation of complex molecules, such as the oxidation of bioactive natural products and drugs, 131-139 (as shown in Scheme 19). These molecules are available commercially. Since they are enantiopure, except 135 and 136 (achiral), PVP and 73 are used separately in the Cu/Au (3:1)/H₂O₂ oxidation reactions. CH₃CN can be used as a co-solvent to dissolve the complex molecules if needed. The products' regiochemistry can be determined by single-crystal X-ray analysis, or 2D COSY, NOSY, HMQC, and HMBC NMR spectroscopy. Notably, the oxidation produces OH or ketone function, which can be converted into amines or oxime for possible enhancement of bioactivity. The assumed oxidative sites are depicted in 131A-139A, and in some embodiments, the resulting alcohols may oxidize further to give the corresponding ketones. The derivatives of abietic acid (131), a diterpene resin acid, have shown a number of bioactivities, including antiallergic and anticonvulsant activities. Dehydroabietylamine (precursor of 132), a pyruvate dehydrogenase kinase inhibitor, and its derivatives have been revealed to inhibit triple-negative breast cancer. Ambroxide (133) or ambroxan is responsible for the odor of ambergris. Estrone (the C3-OH derivative of 134) is an estrogenic hormone and its C16-oxime derivatives have been shown to possess anti-cervix and anti-breast carcinoma activities. Amantadine (the C1-NH₂ analog of 135) is used for Parkinson's disease and Memantine (the C1-NH₂ precursor of 136), an inhibitor of NMDA receptor, is used for the treatment of Alzheimer's disease. Caryophyllene oxide (137) selectively inhibited intestinal cancer cell lines but did not affect the viability of hepatocytes. Oxymatrine (138) inhibits cardiac ischemia and aldosterone-induced cardiac fibroblast proliferation. Artemisinin (139) is an anti-malarial drug and possesses anticancer activity.

Scheme 19 Late-stage C-H oxidation of bioactive molecules using catalytic amount of Cu/Au (3:1)-73 and H₂O₂.

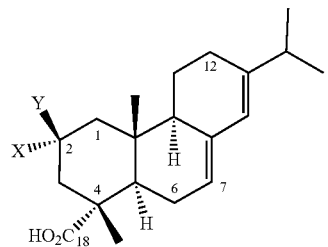

131: X = Y = H; Abietic acid
131A: X = OH; Y = H
131B: X & Y = O

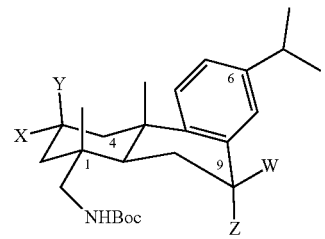

132: X = Y = W = Z = H;
N-Boc-dehydroabietylamine;
132A: X = OH; W = Y = Z = H
132A: W = OH; X = Y = Z = H 133: X = Y = H;
(−)-ambroxide
133A: X = OH; Y = H
133B: X & Y = O 134: X = Y = H
estrone methyl ether
134A: X & Y = O 135: X = Y = H;
N-Boc-1-amino-adamantane
135A: X = OH, Y = H
135B: X & Y = O 136: X = Y = H;
N-Boc-memantine
136A: X = OH, Y = H 137: X = Y = H;
(−)-carophyllene oxide
137A: X & Y = O 138: X = Y = H;
oxymetrine
137A: X = OH, Y = H
137B: X & Y = O 139: X = Y = H;
(+)-artemisinin;
139A: X = OH, Y = H
139B: X & Y = O Nanodelivery of dsRNA Using α-Hydroxy-PVP Polymer α-hydroxy-PVP polymer was synthesized according to Scheme 2, above. The molecular weight of the polymer was determined to be 67,425 by gel permeation chromatography using TSKgel GMHx1 column and water as eluent. To illustrate the encapsulation of dsRNA using α-hydroxy-PVP, a 5% by weight of dsRNA-SFD (112 bp; MW ~72,100) was encapsulated using the polymer in water, and the resulting solution was lyophilized to give a white solid. The size (i.e., 112 bp) of the dsRNA-SFD was designed to target a unique alternative splicing region of the vacuolar H[+]-ATPase SFD subunit gene (VhaSFD) in western corn rootworm (*Diabrotica virgifera virgifera*).

Figure 9:
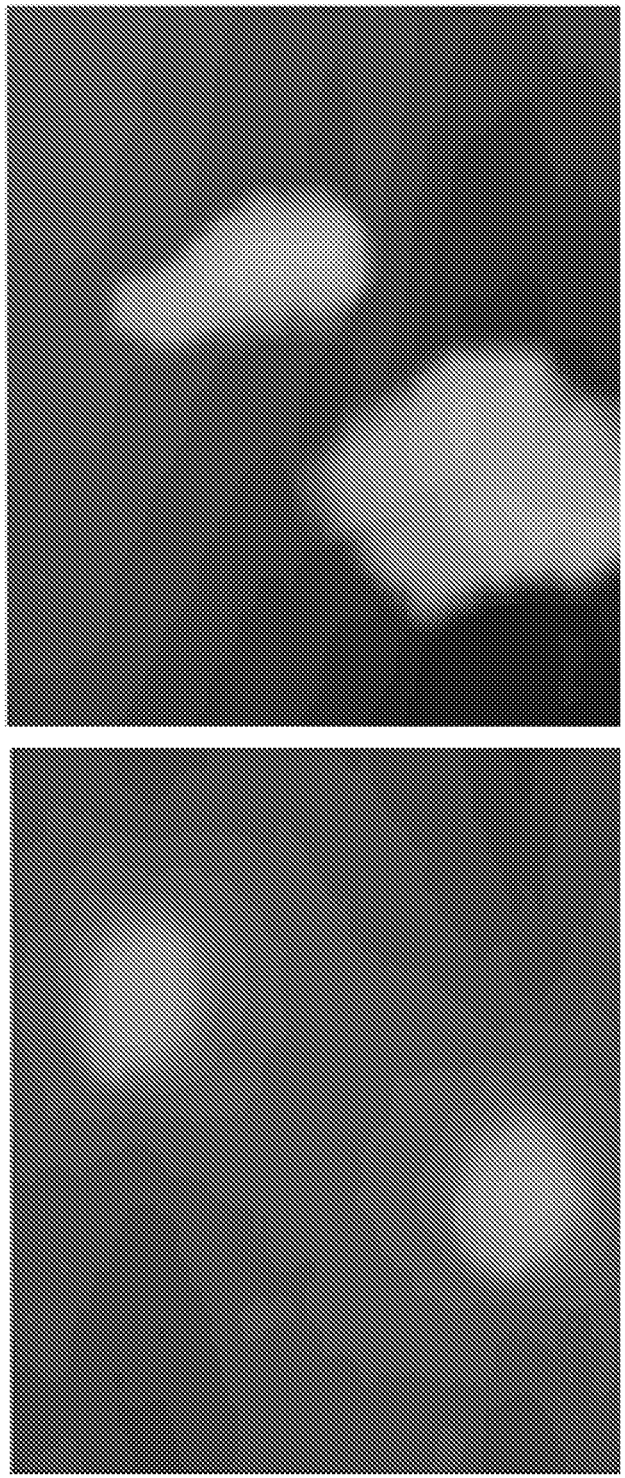
FIG. 9 contains representative AFM images of α-hydroxy-PVP 1 (left panel) showing sizes of 50-60 nm, and encapsulated α-hydroxy-PVP 1 and dsRNA-SFD (right panel) showing sizes of 450×600 nm.

The resulting encapsulated material was studied by atomic force microscopy (AFM) (FIG. 9) and representative images showed that the polymer had a spherical shape with widths of 50-60 nm (FIG. 9 left panel). After encapsulation, the α-hydroxy-PVP/dsRNA nanoparticles exhibited an elongated shape with average diameters of 450×600 nm (FIG. 9 right panel). The AFM images suggested that dsRNA is wrapped around by the polymers producing elongated shapes and larger sizes of nanoparticles.

The α-hydroxy-PVP/dsRNA-SFD encapsulated nanoparticle construct suppressed the transcript level of the target gene (VhaSFD) by >90% after western corn rootworm adults were fed on an artificial diet containing the construct for only two days at 1 g dsRNA per adult.

I claim:
1. A chiral substituted polyvinylpyrrolidinone compound having the formula wherein one of $R^1$ and $R^2$ comprises a functional group having at least 1 carbon atom selected from the group consisting of alcohols, ethers, aliphatic hydrocarbons, aromatic hydrocarbons, and combinations thereof, and the other of $R^1$ and $R^2$ is H or OH, and n is greater than 100.

2. The compound of claim 1, wherein $R^1$ is selected from the group consisting of $CH_2Ph$, $CH_2O$-t-Bu, $CHCH_3CH_3$, $CH_2$(1-Naph), $CH_2OH$, $CH_2OCHPh_2$, and $CH_2OCH(o$-Me-$C_6H_4)_2$, or $R^2$ is selected from the group consisting of OR'

(where R' is an ester or alkyl group), $CH_3$, an alkyl group, $CH_2OH$, and the other of $R^1$ and $R^2$ is H or OH, and n is greater than 250.

3. The compound of claim 1, wherein said compound has a molecular weight of at least 50,000.

4. A chiral substituted polyvinylpyrrolidinone compound comprising an acetonide moiety attached to the pyrrolidine ring.

5. The compound of claim 4, wherein said compound has the formula

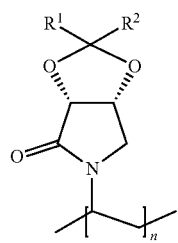

wherein each of $R^1$ and $R^2$ is independently selected from aliphatic or aromatic functional groups, and n is greater than 100.

6. A complex comprising the chiral substituted polyvinylpyrrolidinone compound of claim 1 bound to a core species selected from the group consisting of nanoparticulate materials, proteins, DNA, siRNA, and dsRNA.

7. The complex of claim 6, wherein the complex comprises a nanoparticle cluster.

8. The complex of claim 7, wherein the nanoparticle cluster comprises one or more metals.

9. The complex of claim 8, wherein the nanoparticle cluster comprises one or more metals selected from the group consisting of Au, Pd, Cu, Ce, Mo, Ni, Ru, W, and Fe.

10. The complex of claim 8, wherein the nanoparticle cluster is bimetallic.

11. The complex of claim 6, wherein the bimetallic nanoparticle cluster is selected from the group consisting of Pd/Au, Cu/Au, Ce/Au, Mo/Au, W/Au, Ru/Au, and Fe/Au.

12. The complex of claim 6, wherein the chiral substituted polyvinylpyrrolidinone compound encapsulates the core species.

13. A process for asymmetrically oxidizing organic molecules comprising reacting the organic molecule with one or more reagents in the presence of a complex comprising the chiral substituted polyvinylpyrrolidinone compound of claim 1 bound to a metallic nanocluster to produce chiral molecules.

14. The process of claim 13, wherein the reaction results in the formation of a carbon-carbon bond with the formation of chiral organic molecules.

15. The process of claim 13, wherein the organic molecule is an alkene, the reaction resulting in the oxidation of a carbon-carbon double bond producing chiral diols.

16. The process of claim 13, wherein the organic molecule is selected from the group consisting of cis and trans 1,2-diols and 1,3-diols, the reaction resulting in the oxidation of one hydroxyl group of the organic molecule thereby producing a chiral hydroxyl ketone molecule.

17. The process of claim 13, wherein the reaction oxidizes a carbon-hydrogen bond in the organic molecule to form a chiral alcohol or ketone molecule possessing a hydroxyl or carbonyl functional group.

18. The process of claim 13, wherein the reaction generates a reaction product comprising two enantiomers, and wherein the enantiomeric excess of one of the enantiomers is greater than 50%.

19. The process of claim 13, wherein the reaction generates a reaction product that is enantiopure.

20. The process of claim 13, wherein the reaction generates a reaction product having a hydroxyl or ketone functional group, and wherein the reaction product is further reacted with an organic compound in which the organic compound is added to the reaction product at the site of the hydroxyl or ketone functional group.

21. The process of claim 13, wherein the nanoparticle cluster comprises one or more metals selected from the group consisting of Au, Pd, Cu, Ce, Mo, Ni, Ru, W, and Fe.

22. The process of claim 21, wherein the nanoparticle cluster is bimetallic.

23. The complex of claim 22, wherein the bimetallic nanoparticle cluster is selected from the group consisting of Pd/Au, Cu/Au, Ce/Au, Mo/Au, Ni/Au, W/Au, Ru/Au, and Fe/Au.

* * * * *